United States Patent [19]

Leavitt et al.

[11] Patent Number: 5,160,847
[45] Date of Patent: Nov. 3, 1992

[54] DYNAMIC MULTIVANE ELECTRON ARC BEAM COLLIMATOR

[75] Inventors: Dennis D. Leavitt; George A. Takach, Jr., both of Salt Lake City, Utah

[73] Assignee: The Parvus Corporation, Salt Lake City, Utah

[21] Appl. No.: 346,908

[22] Filed: May 3, 1989

[51] Int. Cl.⁵ ............................................. G21K 1/04
[52] U.S. Cl. .............................. 250/505.1; 250/442.3; 378/152; 378/151; 378/147; 378/65
[58] Field of Search ................... 250/505.1, 492.3; 378/152, 151, 147, 65

[56] References Cited

U.S. PATENT DOCUMENTS 4,868,843  9/1989  Nunan ........................... 250/505.1

OTHER PUBLICATIONS

Leavitt et al., Int. J. Radiation Oncology Biol. Phys., vol. 11, May 1985, pp. 987–999.
McNeely et al., Int. J. Radiation Oncology Biol. Phys., vol. 14, Jun. 1988, pp. 1287–1294.
Leavitt et al., Proceedings of the 9th International Conference on the Use of Computers in Radiation Therapy, Jun. 1987, pp. 149–152.
Leavitt et al., Int. J. Radiation Oncology Biol. Phys., vol. 16, Feb. 1989, pp. 489–496.
Leavitt, Proceedings of the Twelfth Varian Users' Meeting, May 3, 1988, pp. 63–67.
Leavitt et al., "Electron Arc Therapy: Design, Implementation and Evaluation of a Dynamic Multi-Vane Collimator System", 30th Ann. Meeting of the Am. Soc. of Therapeutic Radiation and Oncology, Oct. 11, 1988.

Primary Examiner—Jack I. Berman
Attorney, Agent, or Firm—Jon C. Christiansen; David R. Black; Eleanor V. Goodall

[57] ABSTRACT

This invention is a dynamic multivane electron arc beam collimator having collimation vanes, means for controlling the vanes, and local controllers at the collimation site which dynamically define an electron aperture which defines the electron field of an electron beam emitted by a linear accelerator during electron arc therapy. The collimator can be attached to or detached from the head of a linear accelerator. The collimator provides for improvement in electron arc therapy dose uniformity.

18 Claims, 25 Drawing Sheets

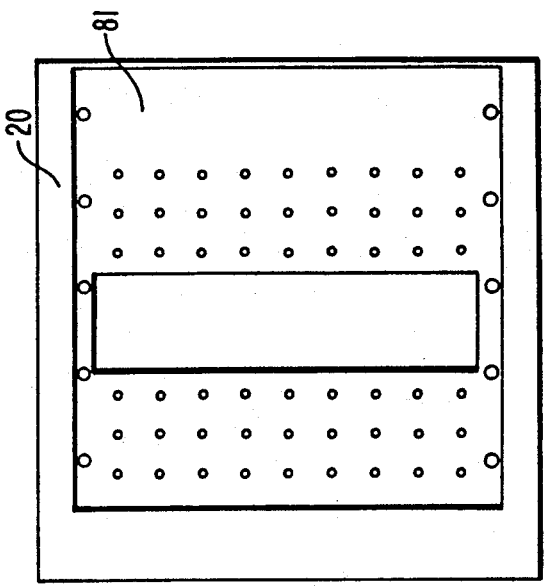
FIG. 10B
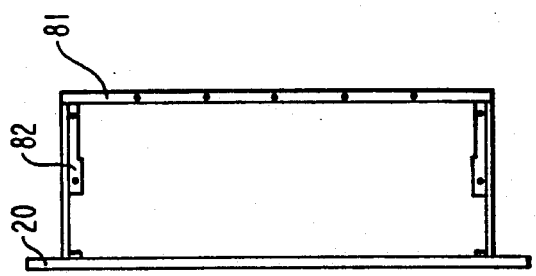
FIG. 10A
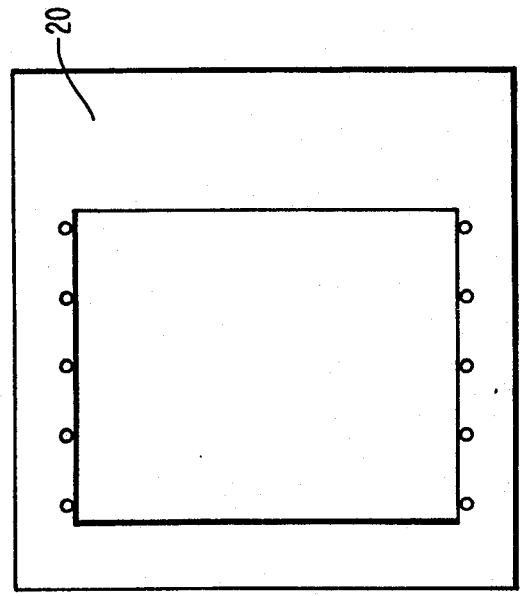
FIG. 10
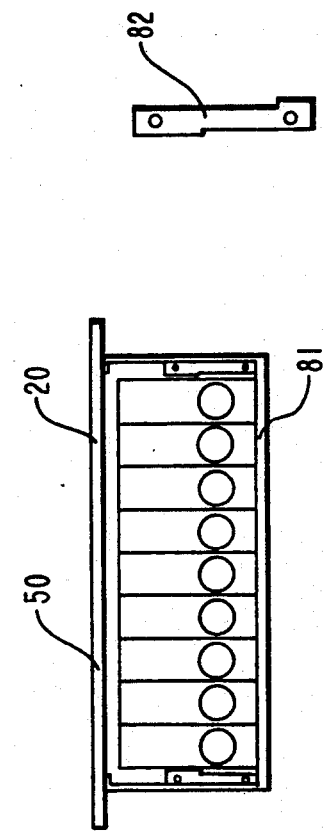
FIG. 10E
FIG. 10D
FIG. 10C

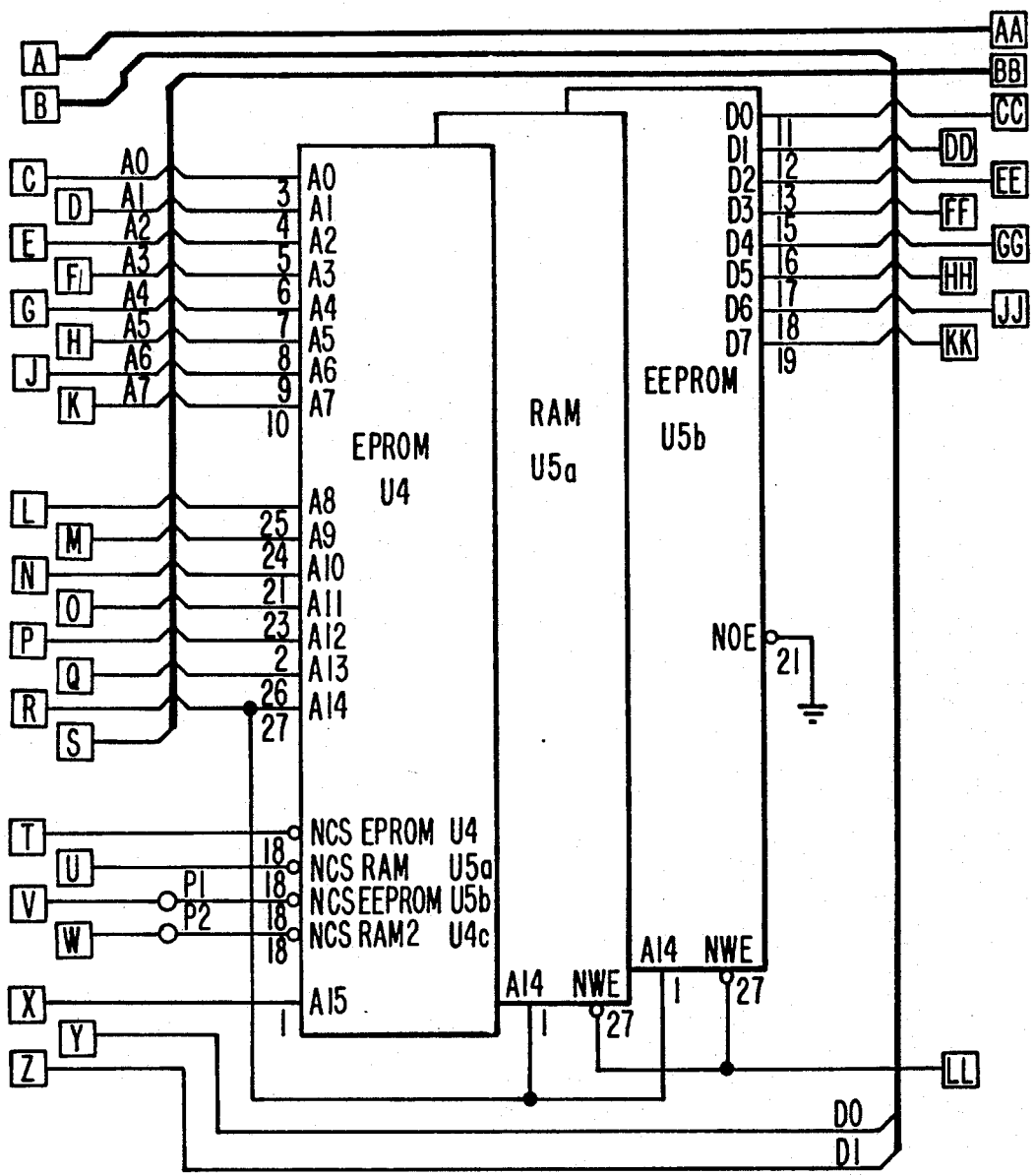
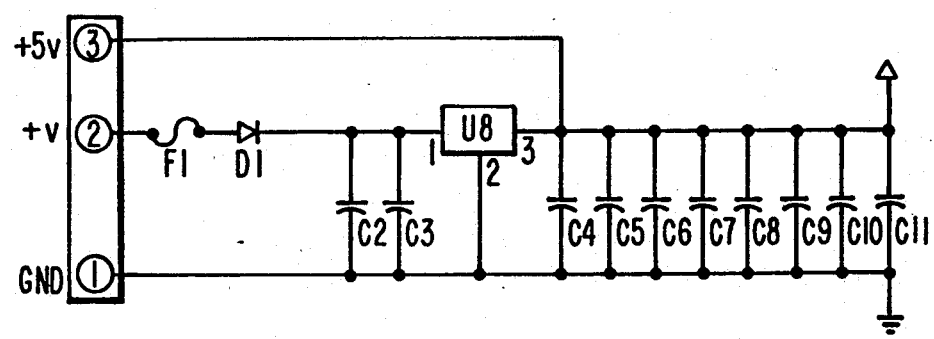
FIG. 16A

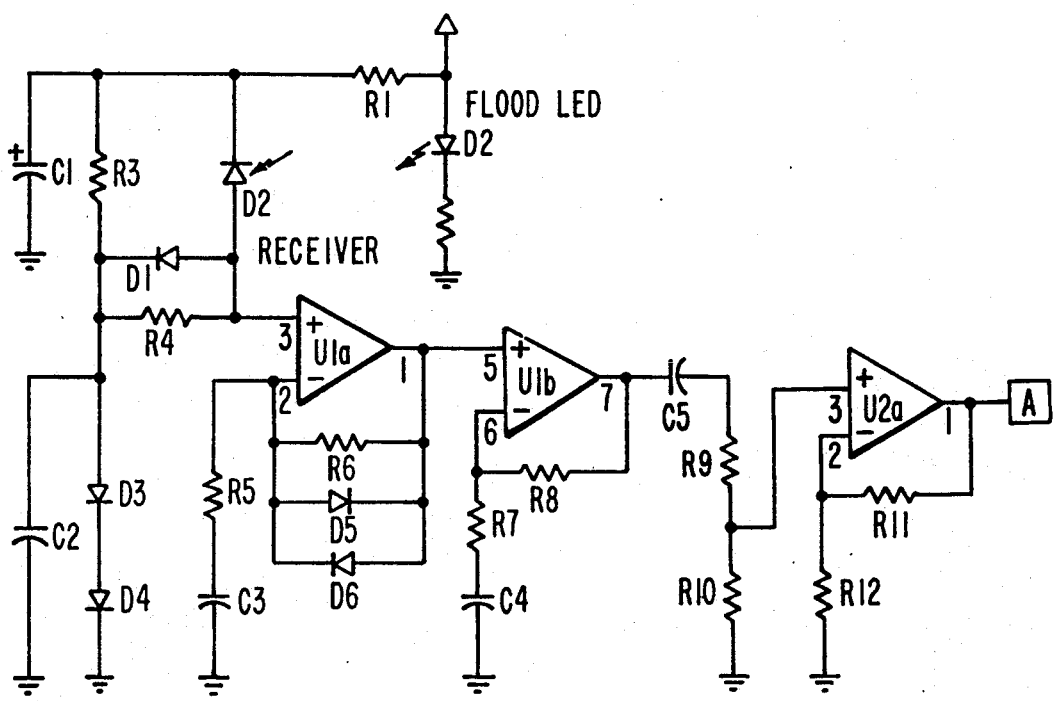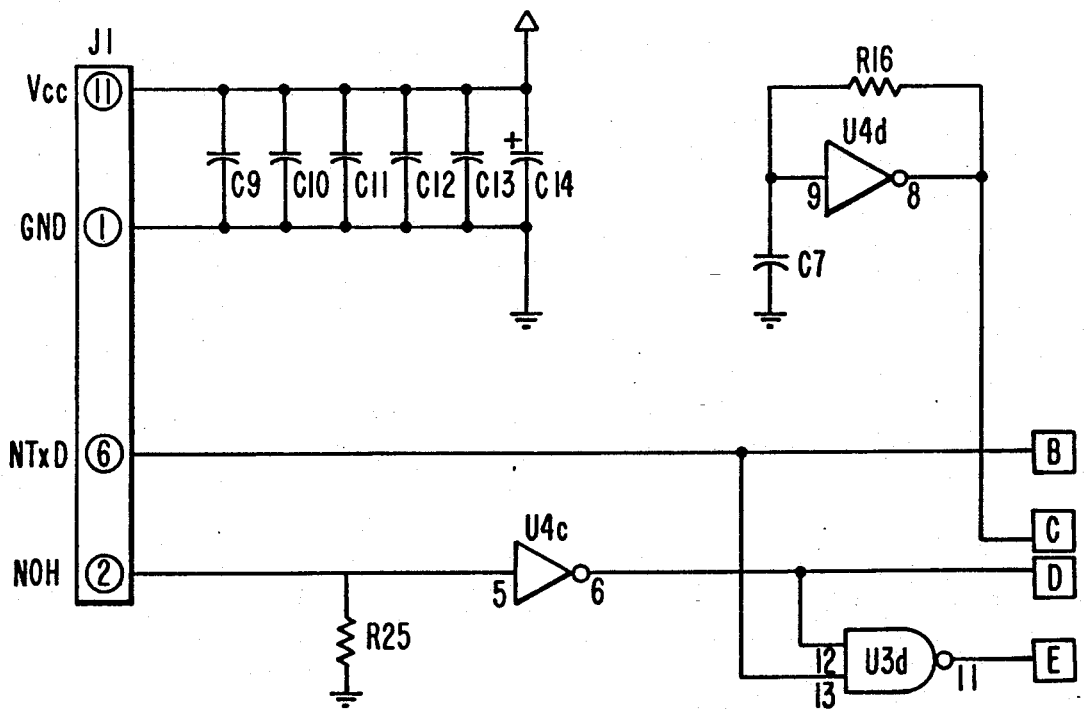
FIG. 19

DYNAMIC MULTIVANE ELECTRON ARC BEAM COLLIMATOR

This invention was made with Government support under grant RAD 5 R01 CA46562 awarded by the National Institutes of Health. The Government has certain rights in the invention.

INTRODUCTION AND BACKGROUND

This invention relates to a dynamic multivane electron arc beam collimator and a dynamic multivane electron arc beam collimation system and related apparatus and methods. The invention is useful in connection with electron arc therapy, which is an electron radiation treatment method used to treat cancer. For example, electron arc therapy is used to treat a patient's chest wall following a mastectomy. The practice of electron arc therapy requires an electron source to provide the electron beam (electron radiation) which is used to treat the target area of the patient. A linear accelerator can be the electron source. A purpose of the invention is to improve the uniformity of dose delivered to a large treatment surface during the technique of electron arc therapy. Dosimetric studies (as detailed in the attached publications list) have shown that an improvement in electron arc therapy dose uniformity can be achieved through application of this invention.

A collimator is used in combination with the linear accelerator to define the shape of the electron field of the electron beam. The shape of the electron field is defined by the collimator's electron aperture. The head of the linear accelerator is moved through or along an arc of rotation above the patient as the electron beam is emitted through the head and collimator to the target area (i.e. treatment area) of the patient. Such movement is referred to herein as "linear accelerator rotation." It is desired that the electron dose be uniform across the target area and that electron radiation to patient areas outside of the target area be minimized.

The following publications include information relevant to an understanding of the invention:

1. Leavitt, D. D., Peacock, L. M., Gibbs, F. A., and Stewart, J. R.: "Electron Arc Therapy: Physical Measurement and Treatment Planning Techniques" *Int. J. Radiation Oncology Biol. Phys.*, Vol. 11, pp. 987-999 (May, 1985).
2. McNeely, L. K., Jacobson, G. M., Leavitt, D. D., and Stewart, J. R.: "Electron Arc Therapy: Chest Wall Irradiation of Breast Cancer Patients" *Int. J. Radiation Oncology Biol. Phys.*, Vol. 14, pp. 1287-1294 (June, 1988).
3. Leavitt, D. D. and Stewart, J. R.: "Optimization of Electron Arc Therapy Doses by Dynamic collimator Control" *Proceedings of the 9th International Conference on the Use of Computers in Radiation Therapy*, pp. 149-152, June 1987.
4. Leavitt, D. D., Stewart, J. R. Moeller, J. H., and Earley, L.: "Optimization of Electron Arc Therapy Doses by Multi-vane Collimator Control" *Int. J. Radiation Oncology Biol. Phys.*, Vol. 16, pp. 489-496 (February, 1989). This paper was presented at the 29th Annual Meeting of the American Society of Therapeutic Radiology and Oncology, Oct. 20, 1987, Boston, Mass.
5. Leavitt, D. D.: "Multileaf Collimation in Electron Arc Therapy". This paper was presented on May 3, 1988 at the Proceedings of the Twelfth Varian User's Meeting.
6. Leavitt, D. D., Stewart, J. R., Moeller, J. H., Lee, W. L., and Takach, Jr. G. A.: "Electron Arc Therapy: Design, Implementation and Evaluation of a Dynamic Multi-vane Collimator System". This paper was presented at the 30th Annual Meeting of the American Society of Therapeutic Radiology and Oncology, Oct. 11, 1988. Accepted for publication in International Journal of Radiation Oncology Bio. Phys. February, 1989.

Copies of the above-identified publications are filed with this patent application and are incorporated by reference into this specification.

Through the innovations of our invention it is possible to design and construct a dynamic multivane electron arc beam collimator that is attachable to the head of a linear accelerator. These innovations contribute to the ease of use of the collimator and reduce the complexity and size of the collimator without reduction of functionality or features. These innovations facilitate collimator installation and eliminate or reduce the need to modify the linear accelerator.

SUMMARY OF THE INVENTION

This invention is a dynamic multivane electron arc beam collimator and a dynamic multivane electron arc beam collimation system.

In one form of this invention, the dynamic multivane electron arc beam collimator includes a plurality of collimation vanes, a plurality of vane movement means associated with the vanes and a plurality of local controllers at the collimation site. The vanes are positioned and adapted to define an electron aperture which defines the electron field of the electron beam emitted by the linear accelerator. The vane movement means move the vanes to dynamically define the electron aperture. The local controllers control the vane movement means. Vane movement is independent of the movement of the other vanes and is capable of movement simultaneously with the movement of other vanes.

In another form of this invention, the collimator includes a plurality of collimation vanes, a means for moving said vanes, and local controllers (i.e. local intelligence) at the collimation site for controlling the vane movement means.

Other aspects of this invention provide to the collimator a local power source (e.g. battery) at the collimation site, a noncontact communications means (e.g. infra-red transceiver), and a network for communication between the local processors (and any other network resident nodes such as the host controller).

The elements of the collimator, i.e., the vanes, vane movement means and local controller(s) together with any local power source or noncontact communications means, can be combined to form a unit that is attachable to, and detachable from, the linear accelerator.

In another form of this invention the inventive collimator is part of a dynamic multivane electron arc beam collimation system which further includes: (i) means for selecting a treatment arc and for dividing the treatment arc into a plurality of arc segments defined by reference angles, (ii) means for determining preferred vane pair openings for each arc segment and for representing said preferred vane pair openings as vane position data for each arc segment; (iii) means for monitoring current treatment angle of the linear accelerator during linear accelerator rotation to detect reference angles when encountered by such rotation, and (iv) means for sequentially transmitting to the local controllers of the collimator the vane position data of each arc segment when the reference angle identifying the arc segment is encountered by linear accelerator rotation. The local controllers of the collimator are adapted to process the vane position data received by the local controllers. The local controllers and vane movement means are adapted to cause the vanes to move to the vane positions represented by the vane position data of the arc segments as transmitted to the local controllers during linear accelerator rotation.

An innovation of this invention is the use of distributed processing as applied to the local controllers of the collimator. A plurality of local controllers is used instead of a single controller at the collimator site. The sum of the complexities and size requirements of a plurality of local controllers for controlling a given number of vanes (or vane movement means) is less than the complexity and size requirement of a single controller for controlling the same number of vanes (or vane movement means). By using a plurality of local controllers the collimator is less complex and smaller than would otherwise be the case. These characteristics contribute to the design and construction of a collimator that can attachable to and detachable from the head of a linear accelerator.

An innovation of this invention is the concept of a dynamic electron beam collimator that is attachable to and detachable from the head of a linear accelerator. Small size and light weight of the collimator make such attribute practicable. Because the collimator of this invention is only intended for electron arc therapy it only needs to be exposed to radiation in the treatment room during its use as an electron arc therapy collimator. When not in use, the collimator can be detached from the linear accelerator and removed from the treatment room to avoid radiation damage to the collimator electronics during other radiation treatment processes. Because of this limited exposure, the collimator does not require the large amount of shielding that would be needed to protect its electronics against the kinds and quantities of radiation that it would necessarily be exposed to if the collimator was permanently attached to the linear accelerator or attached in such a way that it would not be practicable or easy to remove the collimator from the linear accelerator during nonuse. The practice of removing the collimator (which is practicable only if the collimator is removable and portable) to protect it against excessive radiation allows for the use of local intelligence (local controllers) in the collimator to control and monitor vane movement.

An innovation of this invention is the concept of a dynamic multivane electron arc beam collimator that can be used as an accessory to a linear accelerator without the need for modification of the linear accelerator. For example, the collimator can be attached to a conventional linear accelerator by attachment to the standard accessory mount assembly as if the collimator were an accessory tray compatible with the accessory mount assembly of the linear accelerator. Thus, the dynamic collimator can be attached to any linear accelerator in the same manner as fixed collimation plates and blocks.

An innovation of this invention is the concept of a dynamic multivane electron arc beam collimator that can be operated independent of any electrical connection to the linear accelerator. The collimator can function as a self-contained unit independent of the electronics of the linear accelerator. This simplifies the task of installing the collimator and/or retrofitting the linear accelerator for use with the dynamic collimator.

An innovation of this invention is the application of local intelligence (local controllers) to the dynamic collimator at the collimation site. This contributes simplicity of use and facilitates after market installation to linear accelerators. Local intelligence at the collimation site eliminates the need for connections (e.g. cables) to a remote source of intelligence (i.e., a remote controller). Local intelligence also allows device function verification and testing to be performed prior to any treatment cycle.

An innovation of this invention is the concept of a local power source (e.g. battery) at the dynamic collimation site. This eliminates the need for connections (e.g. cables) to a remote power source.

An innovation of this invention is the concept of noncontact communication between the local controllers at the dynamic collimation site and a collimator controlling host computer. This eliminates the need for physical connections (e.g. cables or wiring) running from the dynamic collimator to the collimator controlling host computer. This simplifies the task of installing the collimator and/or retrofitting the linear accelerator for use with the dynamic collimator.

An innovation of this invention is the concept of applying network communications to the local controllers at the dynamic collimation site and the other intelligent devices (e.g., host controller, display monitors, etc.). The use of a network (e.g. token passing network) for communications facilitates the addition of additional vanes, sensors, controllers, monitors and other devices that may be desired by the user.

The above-identified innovations are included in the embodiment of this invention described in detail below but such innovations and this invention are not limited to such embodiment.

This invention further includes the other innovations, improvements and novel apparatus and methods disclosed elsewhere in this disclosure and/or the accompanying drawings.

BRIEF DESCRIPTION OF THE DRAWINGS

FIG. 1 further depicts the computers and monitors in a control room.

FIGS. 10, 10A, 10B, 10C, 10D, and 10E depict a collimator housing including Bottom View, Front View, Top View, Side View, Back View and Side Bracket, respectively. The Bottom View is a view of the bottom plate shown as a maintenance plate.

FIGS. 16, 16A, and 16B depict the electrical schematic of a local controller.

FIGS. 19 and 19A depict the electrical schematic of an infra-red transceiver.

Figure 1:
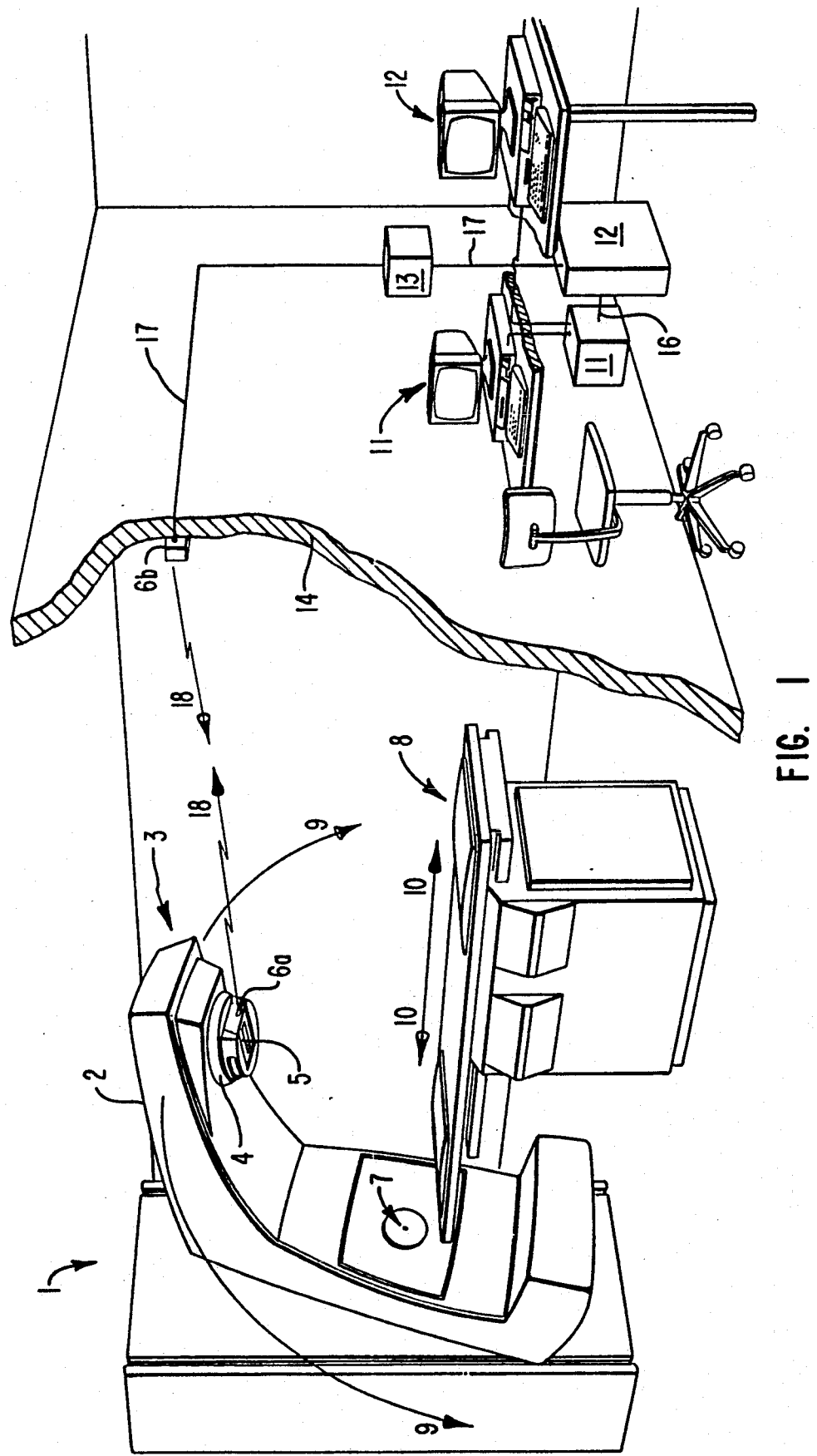
FIG. 1 depicts a linear accelerator, a dynamic multivane electron arc beam collimator and a patient table in the radiation therapy room.

Any numerical dimensions given in the drawings are given in inches.

DETAILED DESCRIPTION OF INVENTION

FIG. 1 depicts a linear accelerator 1 in a radiation therapy or treatment room. The linear accelerator is a source of electrons for electron arc therapy. In this example, the linear accelerator is a Varian Clinac 2100C linear accelerator manufactured by the Varian Radiation Division of Varian Associates, Inc. of Palo Alto, Calif. Other linear accelerators can be used in the practice of this invention. Other manufacturers of linear accelerators include Siemens and Phillips. Linear accelerator 1 includes gantry 2 and head 3. Linear accelerator head 3 includes accesory mount assembly 4. Dynamic multivane electron arc beam collimator 5 is mounted within the accessory mount assembly 4. Linear accelerator gantry 2 is rotatable about a fixed axis of rotation defined by point 7. This gantry rotation provides for rotational movement of the head 3, mount 4 and collimator 5 about patient table 8 as shown by arrows 9. Arrows 9 indicate what is referred to herein as rotation of head 3, mount assembly 4 and/or collimator 5 through or along the arc of rotation or treatment arc. Such movement is also referred to as linear accelerator rotation.

Patient table 8 is used to support the electron arc therapy patient. Patient table 8 is adjustable as indicated by arrows 10 to position the target area (i.e. treatment area) of the patient to receive the electron beam from linear accelerator 1 through head 3 and collimator 5. Collimator 5 includes an electron aperture which dynamically defines the electron field of the beam emitted by linear accelerator 1.

FIG. 1 further depicts computer 11 and computer 12 in a control room. Computer 11 is used for control, operation and monitoring of the linear accelerator and represents conventional hardware and software typically used by users of the Varian Clinic 2100C linear accelerator. Computer 12 is an IBM PS/2 Model 80 system (or other computer system) that runs the Collimator Treatment Conversion Program and Remote Collimator Control Program described below. Monitor 13 is a local display panel used to display actual collimator vane positions through nine numerical displays indicating percentage of opening for each of the nine dosage planes defined by the collimator vanes.

Linear accelerator 1 and patient table 8 are separated from computers 11 and 12 and monitor 13 by wall 14 (i.e. they are in separate rooms). This separation provides protection (i.e. shielding from electron radiation) to the operators in the computer control room.

Figure 2:
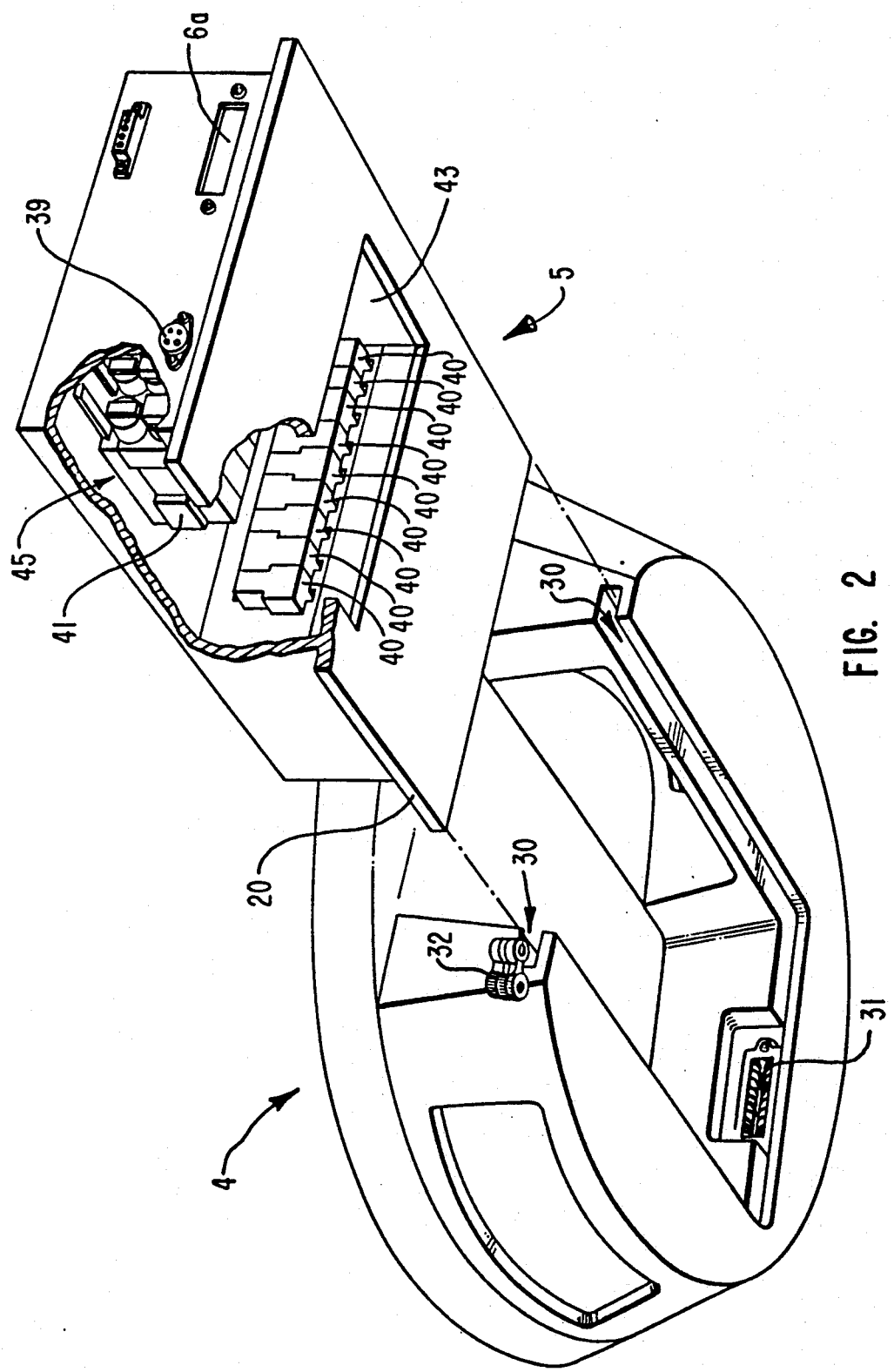
FIG. 2 depicts a dynamic multivane electron arc beam collimator and an accessory mount assembly into which the collimator is inserted for attachment to the linear accelerator head.

FIG. 2 depicts collimator 5 which is attachable to the linear accelerator head 3 by attachment to accessory mount assembly 4. The housing of Collimator 5 includes a bottom plate 20 which includes an extension which is insertable into accessory tray groove 30. The standard accessory connector 31 is not used because the collimator 5 operates independently of any electrical connection to linear accelerator 1. Accessory connector 31 could optionally be used to provide power and communication to collimator 5 thus eliminating the need for local power (e.g. local battery) and/or communications (e.g. infra-red transceiver). After insertion of collimator 5 into accessory mount assembly 4, latch 32 is closed to secure collimator 5 in place. In this manner collimator 5 is inserted into accessory mount assembly 4 and attached to the linear accelerator head 3. Accessory mount assembly 4 is standard equipment with the Varian Clinac 2100C and accepts a wide variety of accessory trays, including, for example, fixed collimators. Through the technology of this invention, a dynamic electron beam collimator (i.e. collimator with a dynamically configurable electron aperture) can be sized and adapted to utilize the standard accessory mount assembly of the linear accelerator without any electrical connection to the linear accelerator.

Figure 4:
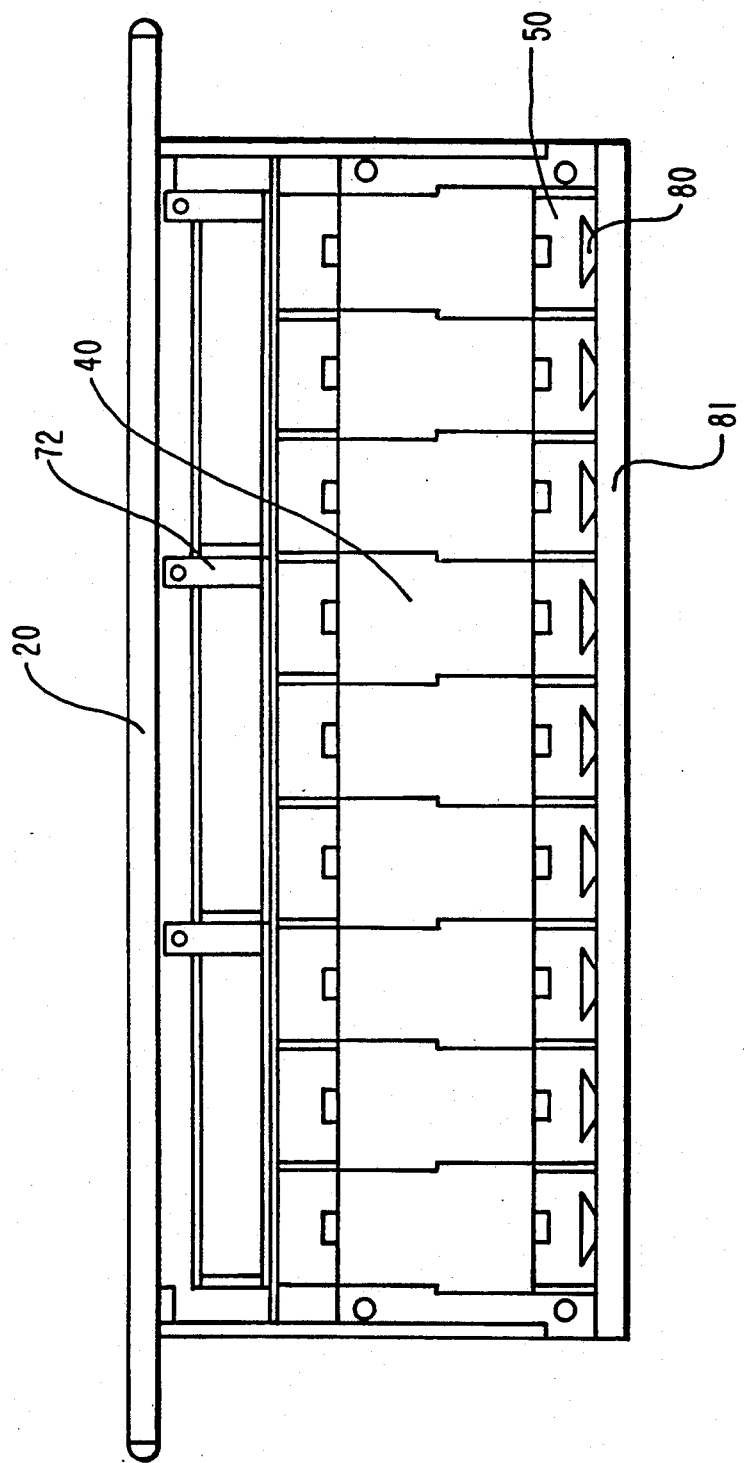
FIGS. 4, 4A, and 4B depict the vanes of a dynamic multivane electron arc beam collimator including a Bottom View, an Exposed End View and Vane Location Detail, respectively.
Figure 4A:
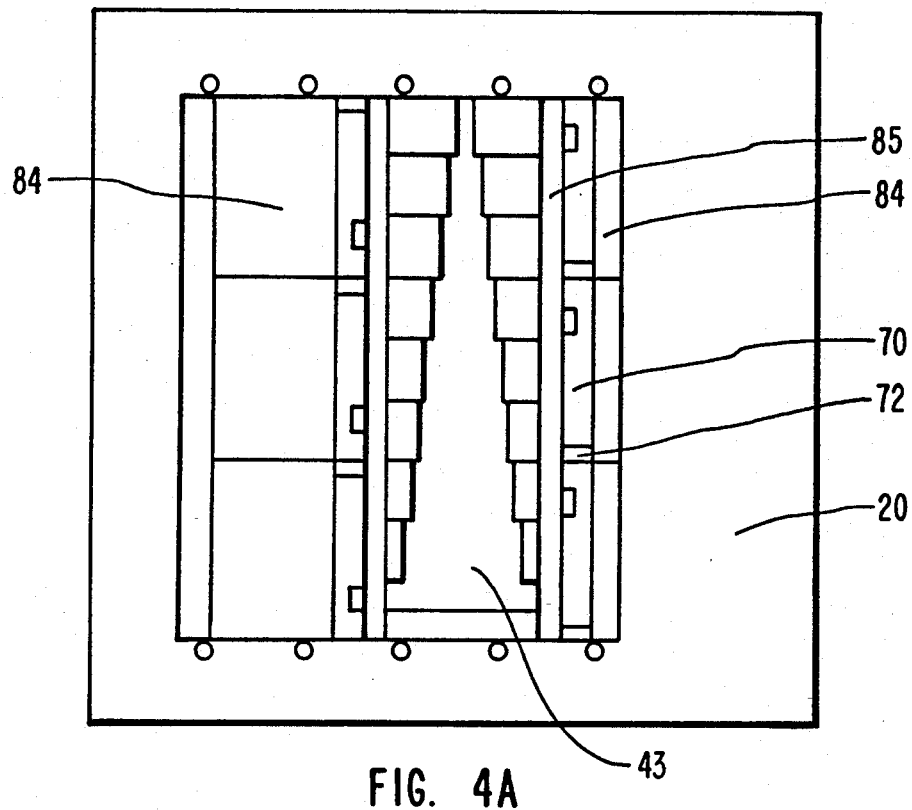
Figure 4B:
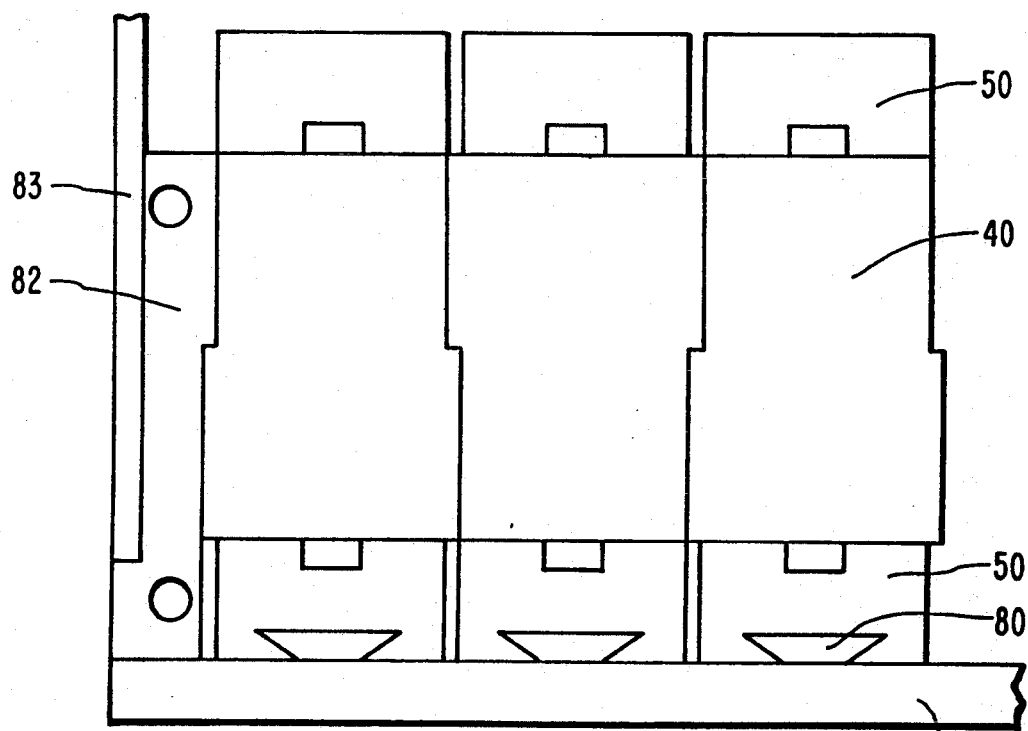

Collimator 5 as shown in FIG. 2 includes brass collimation vanes 40 and 41. The numeral 40 represents nine vanes positioned in a row. The numeral 41 represents nine other vanes positioned in a second row parallel to the first row of vanes 40. Only part of one vane 41 is shown in FIG. 2. Vanes 41 are positioned opposite vanes 40. Each vane 40 has a corresponding opposite vane 41. Each such vane pair (i.e. pair of opposite vanes) defines a dosage plane, i.e., rotation of the vane pair through the arc of rotation (the selected treatment arc) defines a plane. The vanes 40 and 41 and the opening 43 in bottom plate 20 (a clinical use bottom plate) define the electron aperture. The electron aperture can be dynamically defined or configured (i.e., the aperture shape can be changed) by movement of the vanes 40 and 41. A vane movement means causes each vane to move linearly (i.e. along a single axis). Each vane can be caused to move towards or away from its opposite vane counterpart. The Bottom View in FIG. 4 shows two rows of vanes through the opening in the bottom plate (maintenance plate) of the collimator housing. At one extreme, the two opposing vanes have been moved towards each other as close as the vane movement means will permit and define a minimum ("MIN") aperture or opening between the two vanes. In this embodiment of the invention the minimum opening is 0.450 inches. At the other extreme shown in the Bottom View of FIG. 4, the two opposing vanes have been moved as far away from each other as the vane movement means will permit and define a maximum ("MAX") aperture or opening between the two vanes. In this embodiment of the invention the maximum opening is 2.30 inches. In the Bottom View of FIG. 4, the remaining seven vane pairs have been caused by the vane movement means to assume various intermediate positions and to thereby define various intermediate apertures or openings. The electron aperture is defined and shaped by the apertures or openings defined by the vane pairs. A separate vane movement means is associated with each vane. Both asymmetric and symmetric motion of each vane of the vane pair is allowed. The vane movement means provides for simultaneous and independent movement of each vane, i.e., each vane can be moved independent of the movement of the other vanes and each vane can be moved simultaneously with the movement of other vanes. Such movement occurs during rotation of the linear accelerator head 3 and collimator 5 through a selected arc of rotation or treatment arc (see arrows 9) as shown in FIG. 1. As the collimator 5 is rotated through the treatment arc the vanes can be moved by their respective vane movement means to appropriate vane positions. In this manner the electron aperture is dynamically defined or configured (i.e. changed) as the head 3 and collimator 5 move through the treatment arc of rotation. Such dynamic configuration or shaping of the electron aperture (and, therefore, the electron field) allows for greater uniformity in electron radiation dosage of the patient's target area and reduces electron radiation to areas outside of the target area. The movement of a vane pair through the selected treatment arc of rotation defines a dosage plane. The nine vane pairs define nine dosage planes which are parallel to each other and to the plane defined by gantry rotation.

In this embodiment of the invention 9 vane pairs (18 vanes) are used. This number of vane pairs can be varied in the practice of this invention. Typically the number of vane pairs will be within the range of 3 to 71. The preferred number of vane pairs ranges from 5 to 31. An odd number of vane pairs is preferred because this provides a center vane pair which is desirable because the patient or target treatment area is easily located and centered with respect to the center vane pair.

The vanes 40 and 41 can be constructed of brass or other material suitable to provide shielding against the electrons emitted by the linear accelerator. Dimensions and details concerning the vanes in this embodiment of the invention are shown in FIG. 4. Associated with each vane is a separate vane movement means. Each vane can be moved independently of the other vanes and simultaneously with the movement of any other vane(s).

Figure 3:
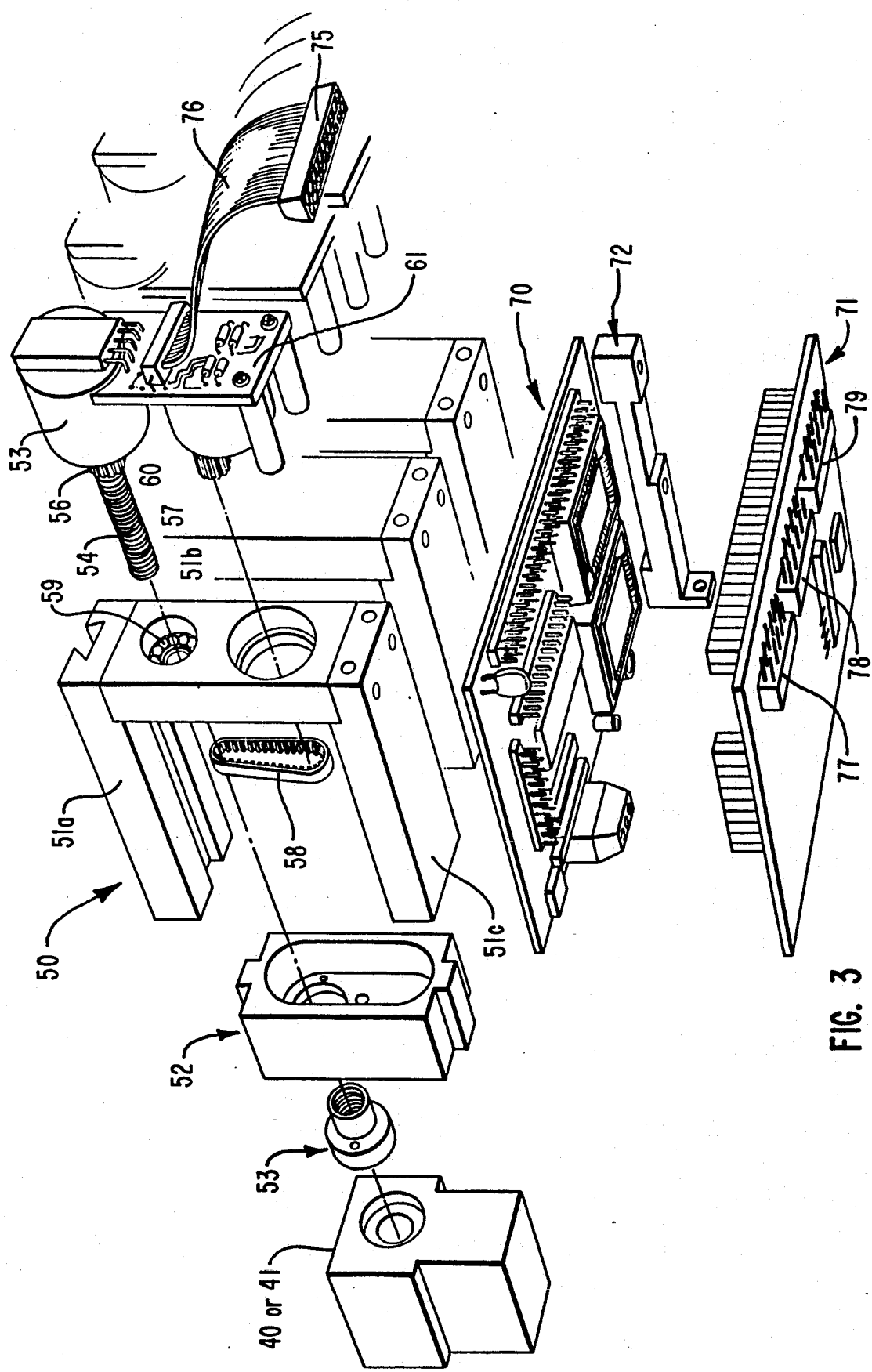
FIG. 3 depicts a vane, a vane assembly, a local controller board and a local controller interface board.

The vane movement means in this embodiment of the invention is a vane assembly 45 (see FIG. 2). A separate vane assembly is associated with each vane 40 or 41. FIG. 3 depicts a vane assembly and its relationship to vane 40 or 41. The vane assembly includes sliding assembly 50, sliding plate 52, floating nut 53, worm screw 54, gear motor 55, geared pulleys 56 and 57, toothed timing belt 58, bearing 59, potentiometer 60 and circuit board 61. These components are assembled together in the manner and arrangement suggested by FIG. 3. The sliding assembly 50 is comprised of aluminum plates 51a, 51b and 51c which are bolted together. Vane movement is accomplished through gear motor 55 which drives (rotates) worm 54 (an 8 pitch brass screw assembly) which in turn causes vane 40 or 41 to move linearly to the desired vane position. Gear motor 55 is a 12000 RPM motor gear reduced 58 to 1. Gear motor 55 and worm 54 can cause vane 40 or 41 to move toward or away from its opposite vane. Full scale single vane movement of 0.925 inches can be accomplished in 2.3 seconds. Each vane is simultaneously monitored and controlled by an absolute means to a resolution of 4 mils. Potentiometer 60 serves as a vane position monitoring means. In this embodiment of the invention the potentiometer is an absolute positioning potentiometer (hybriton element ⅞" dia. 10,000 ohms res.) Proper vane movement (i.e. movement to the correct vane position) is monitored by the potentiometer 60. The potentiometer 60 provides feedback to its associated local controller as well as vane physical limit information to the drive circuitry. The local controller (i.e. three-axis processor) cannot drive the vane beyond its physical stops which are metal pins used to define a minimum opening of 0.450 inches between vanes in a vane pair and a maximum opening of 2.30 inches between vanes in a vane pair. Minimum and maximum vane openings (i.e. the width of the opening between the vanes of a vane pair) can be assigned different values as desired by the practitioner of this invention. The worm 54 is physically attached by set screw to the potentiometer 60 through toothed timing belt 58 which operates in conjunction with geared pulleys 56 and 57. This minimizes the modes of possible failure. False vane movement can only be indicated to the controller by the failure of the floating nut 53 attached to the vane itself. This floating nut is made of Delrin 500 or another sufficiently strong material to reduce the possibility of failure. Motor current trends are also monitored by the potentiometer for possible failure.

Figure 14:
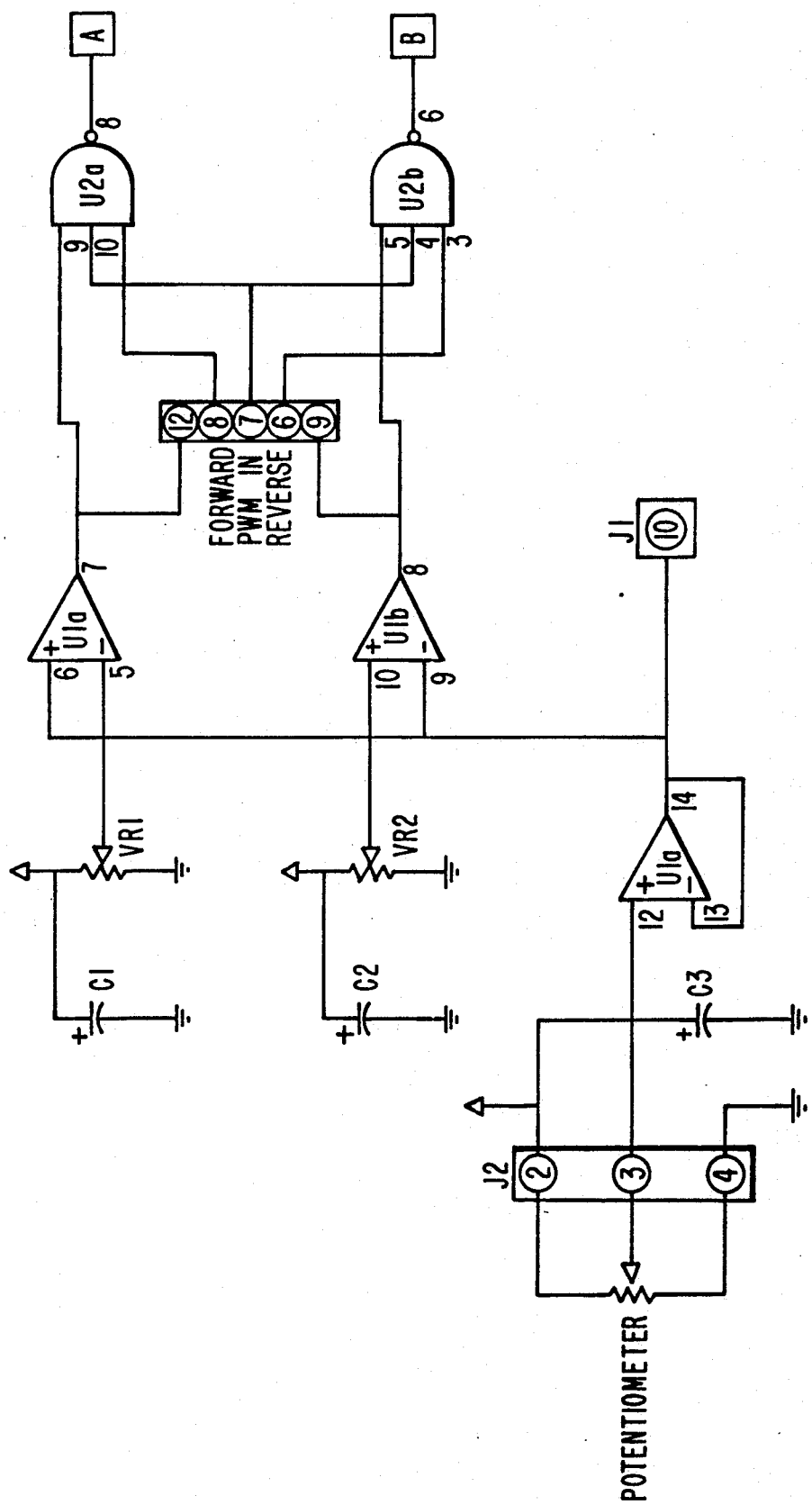
FIGS. 14 and 14A depict the electrical schematic of the circuit board which provides the drive electronics for the gear motor.
Figure 14A:
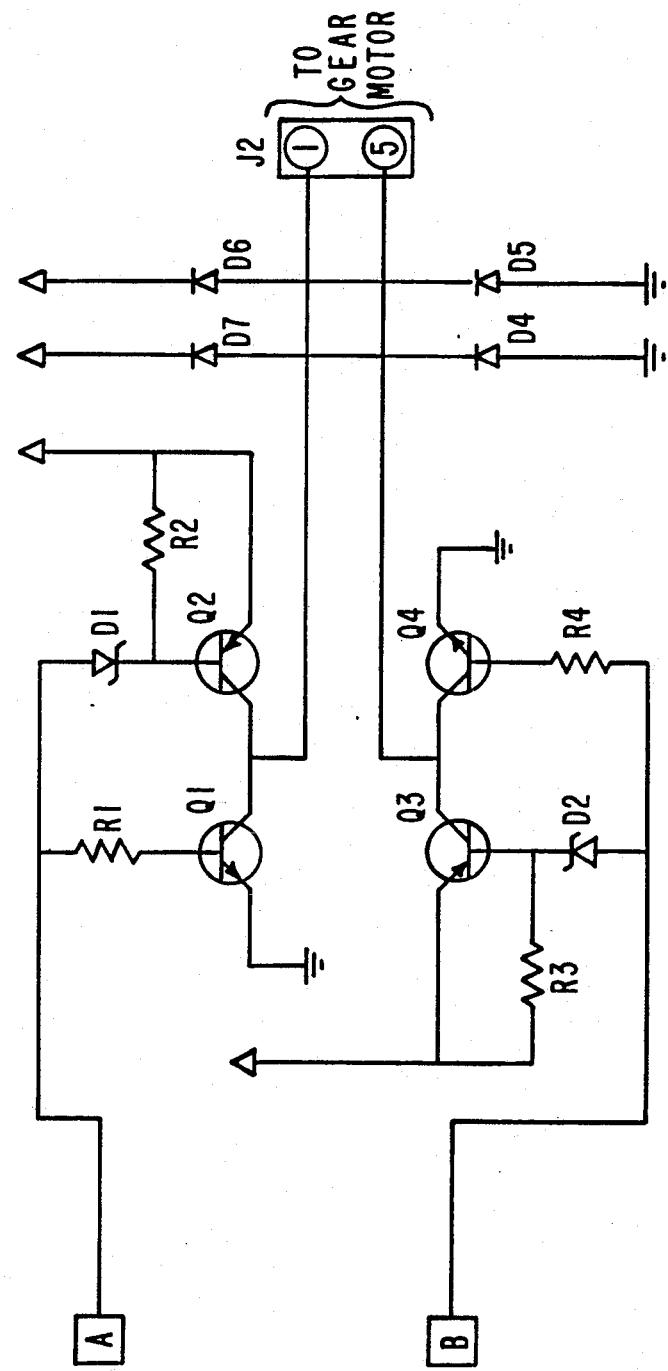
Figure 15:
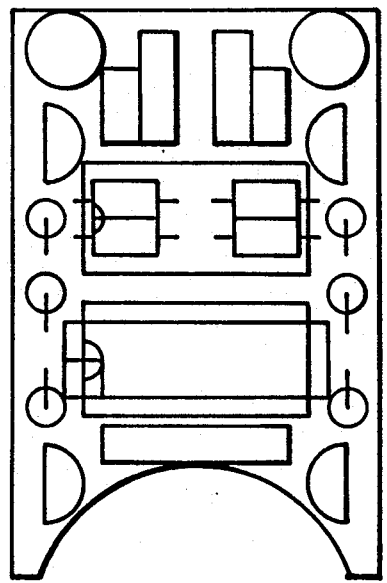
FIGS. 15, 15A, and 15B depict the placement of components on the circuit board of FIG. 14.
Figure 15A:
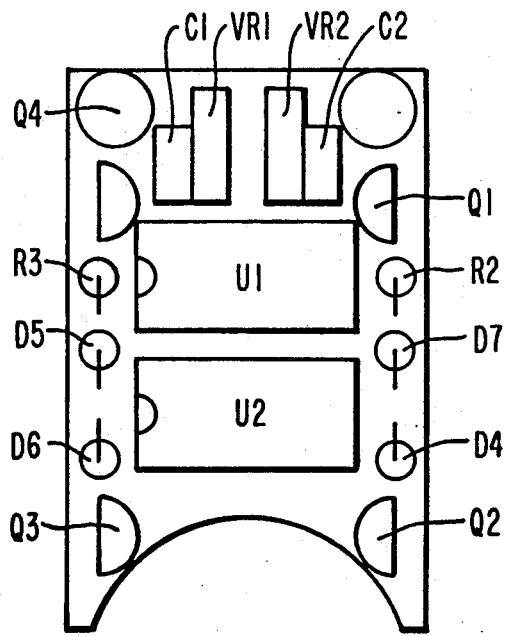
Figure 15B:
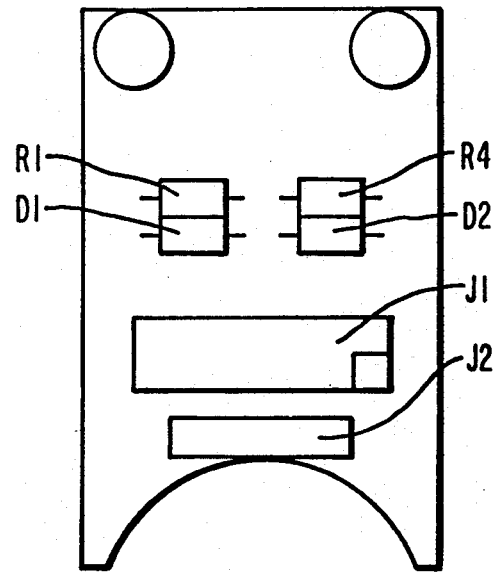

Circuit board 61 provides the drive electronics for the associated gear motor 55 and vane 40 or 41. The circuit board 61 provides H-drive motor circuitry for full four-quadrant drive and control capability. FIG. 14 depicts an electrical schematic of circuit board 61. FIG. 15 depicts the placement of components on circuit board 61. A list and description of these components are set forth below as Table 1:

TABLE 1

Component List - FIGS. 14 and 15

| Location | Manufacturer P.N. Manufacturer | Description |
|---|---|---|
| BD1 | PCB-0034B-01 parvus | Vane Assembly Motor Drive pcb |
| C1, C2 | C320C104K5R5CA Kemet | Ceramic dipped 100 v capacitor .1 ufd |
| D1, D2 | 1N960A Motorola | ½ watt zener diode |
| D4–D7 | 1N914 SEM | small signal diode-fast recovery |
| J1 | 68016-1-5 Dupont | sng row rt agl ml hdr .10" grid 5 × 1 pos |
| Q2, Q3 | MPS6727 Motorola | 1w TO-92 genl purpose PNP hi current transistor |
| Q4, Q1 | MPS6715 Motorola | 1w TO-92 genl purpose NPN high current transistor |
| R1–R4 | RC05GF103J Resistors | 10K ¼ watt resistor |
| U1 | LM324N Motorola | quad 5 v compensated op amp |
| U2 | MC74HC10N Motorola | triple input NAND gate |
| VR1, VR2 | 3292X-1-102 Bourns | 1K ¼" sq. potentiometer, multiturn, trimmer |

Figure 8:
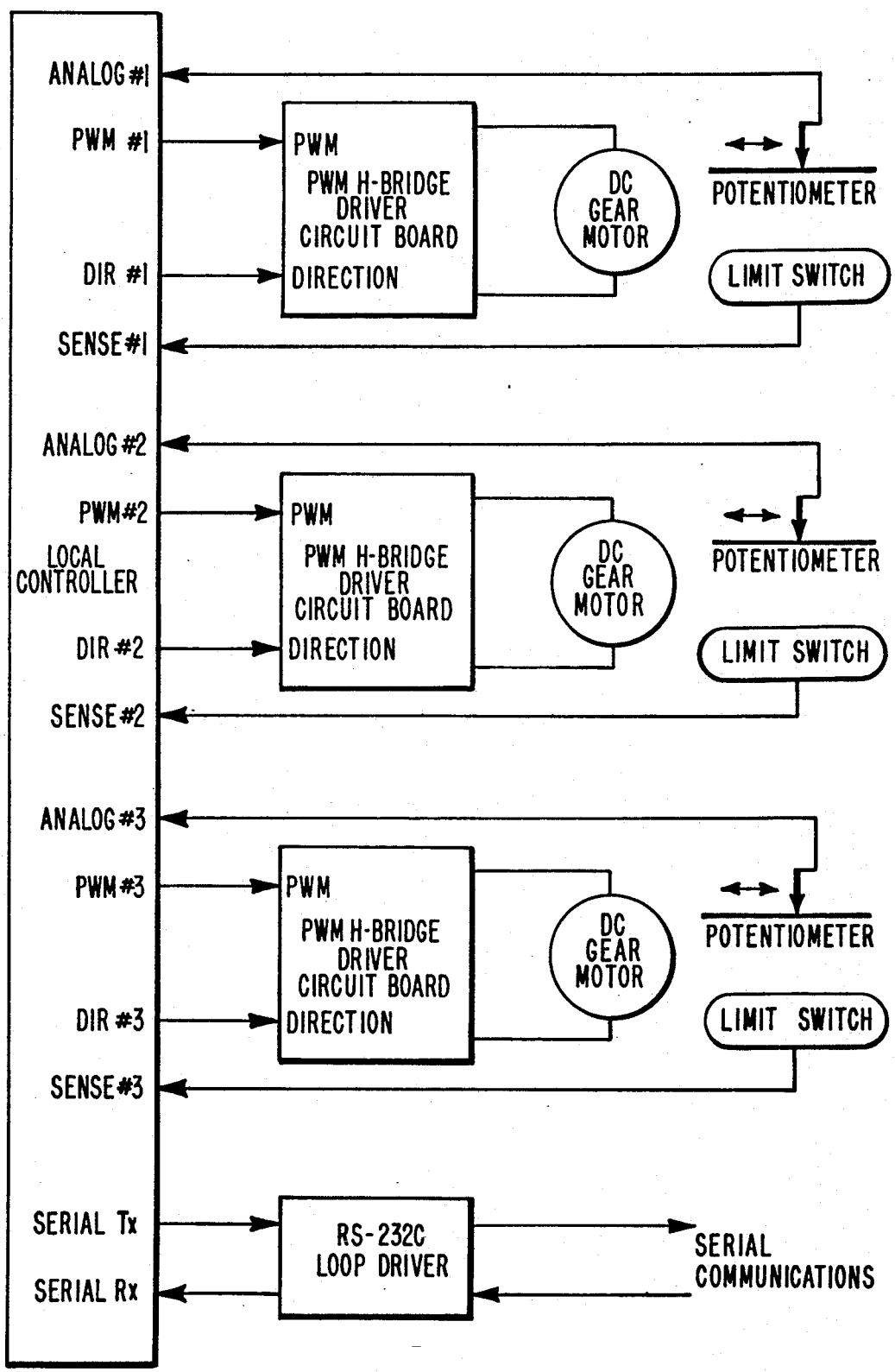
FIG. 8 depicts a Three-Axis Processor Block Diagram.
Figure 12:
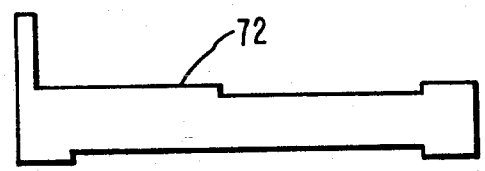
FIGS. 12, 12A, and 12B depict a local controller bracket and a lower collimation bracket.
Figure 12A:
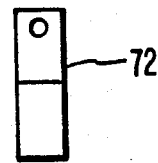
Figure 12B:
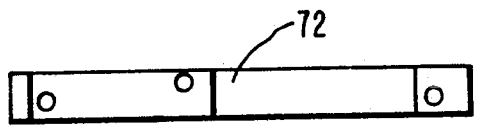
Figure 13:
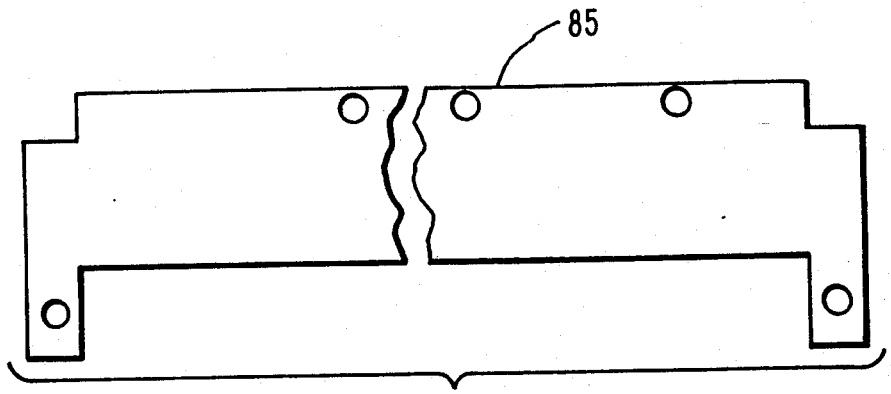
FIGS. 13, 13A, and 13B depict a single vane assembly.
Figure 13A:
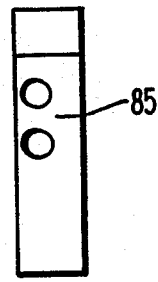
Figure 13B:
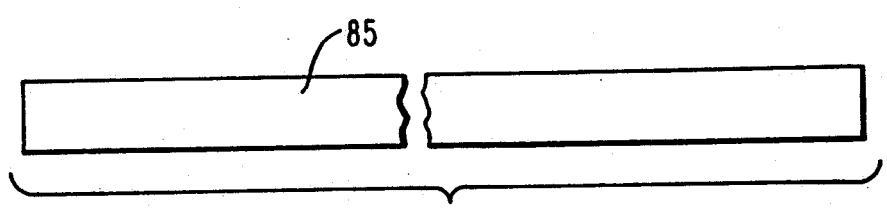

FIG. 3 also depicts local controller 70 and local controller interface 71. A local controller bracket 72 connects local controller 70 and local controller interface 71 by bolts to the lower collimator bracket (see FIG. 12). The collimator includes six local controllers (and six local controller interfaces). Each local controller is a three-axis processor. In this embodiment of the invention each local controller is a four-axis processor manufactured by the parvus Corporation. However, because the fourth axis is inactive in this application the parvus four-axis processor functions as a three-axis processor. For this reason, the local controller of this embodiment of the invention may be described herein as a three-axis processor. Each local controller (i.e. three-axis processor) controls and monitors three vanes. Each axis of the three-axis processor is dedicated to the control of a single vane. Thus the 18 vanes are controlled by six three-axis processors. As shown in FIG. 3, a vane assembly is connected to local controller 70 through local controller interface 71. The vane assembly connects to local controller interface 71 by connecting ribbon cable 76 and ribbon cable plug 75 to ribbon cable receptacle 77. In a similar manner, two other vane assemblies can be connected to ribbon cable receptacles 78 and 79 for control by local controller 70. The other five local controllers are connected to the other fifteen vane assemblies through local controller interfaces in a similar manner. FIG. 8 depicts a functional block diagram of the connections between a local controller and the circuit board 61 of each of the three vane movement means (i.e. vane assemblies) controlled by the local controller. The local controller is based on a standard parvus Node product the multi-purpose ParvNET Node. It is used unmodified except for the Local Controller Software embodied in the onboard 64K bytes of EPROM. The Local Controller has a local processor with a full module bus interface including analog input capability, an internal watchdog system, 32K RAM, 64K serial port with a (serial hardware protocol driver) port, and memory expansion to 192K bytes. The node can handle exception stacking with time tagging on up to 1000 packets. All features of the parvNET PROTOCOL STANDARD (STD-003×-01) are implemented in the on-board software. An 8 Mhz 68HCll processor is used to control all functions and execute the enhanced 6801 code set 68CHll.

The application of distributed processing to the local controllers in an innovation of this invention. Such distribution processing is described below for this embodiment of the invention. A plurality of local controllers are used to distribute the collimator processing load for simultaneous independent motion of all eighteen vanes. Each of the local controllers is uniquely assigned to a separate grouping of three vanes (i.e. a separate grouping of three vane movement means). One local controller handles all required processing and communications for its assigned three vanes. That local controller processes information independent of all other controllers. By distributing the processing over multiple local controllers, efficiency of operation is increased and overall controller complexity and size are reduced. Multiple local controllers require less space than one local controller of equivalent processing power for controlling the same number of vanes. Distributed processing also provides a completely independent means of error detection, critical to clinical use of dynamic collimators. Once a system for distributed processing inside a collimator has been established, future enhancements and future additions are easily accomplished. One future addition can be a secondary level of collimator vane verification.

Figure 16:
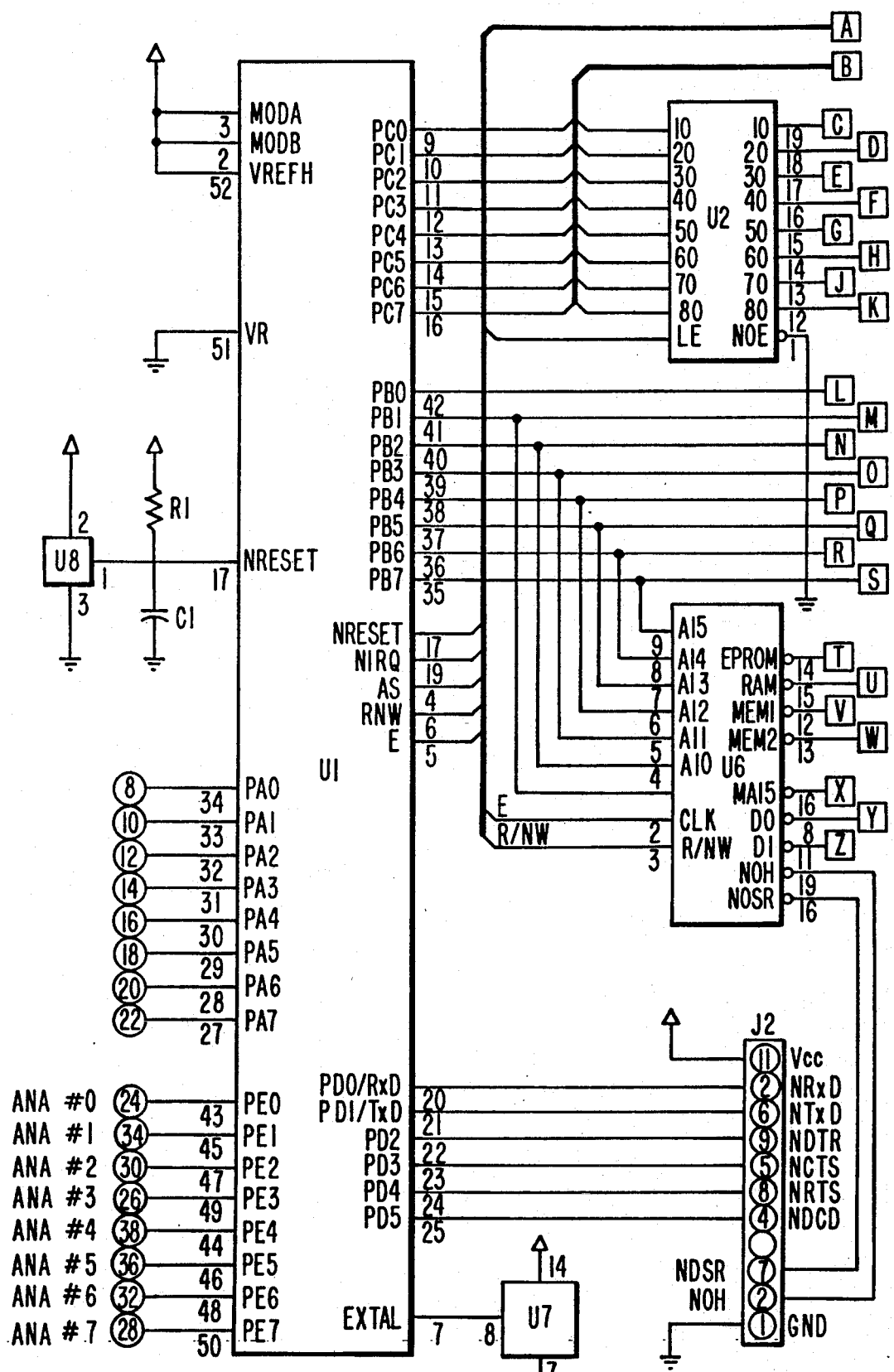
Figure 16B:
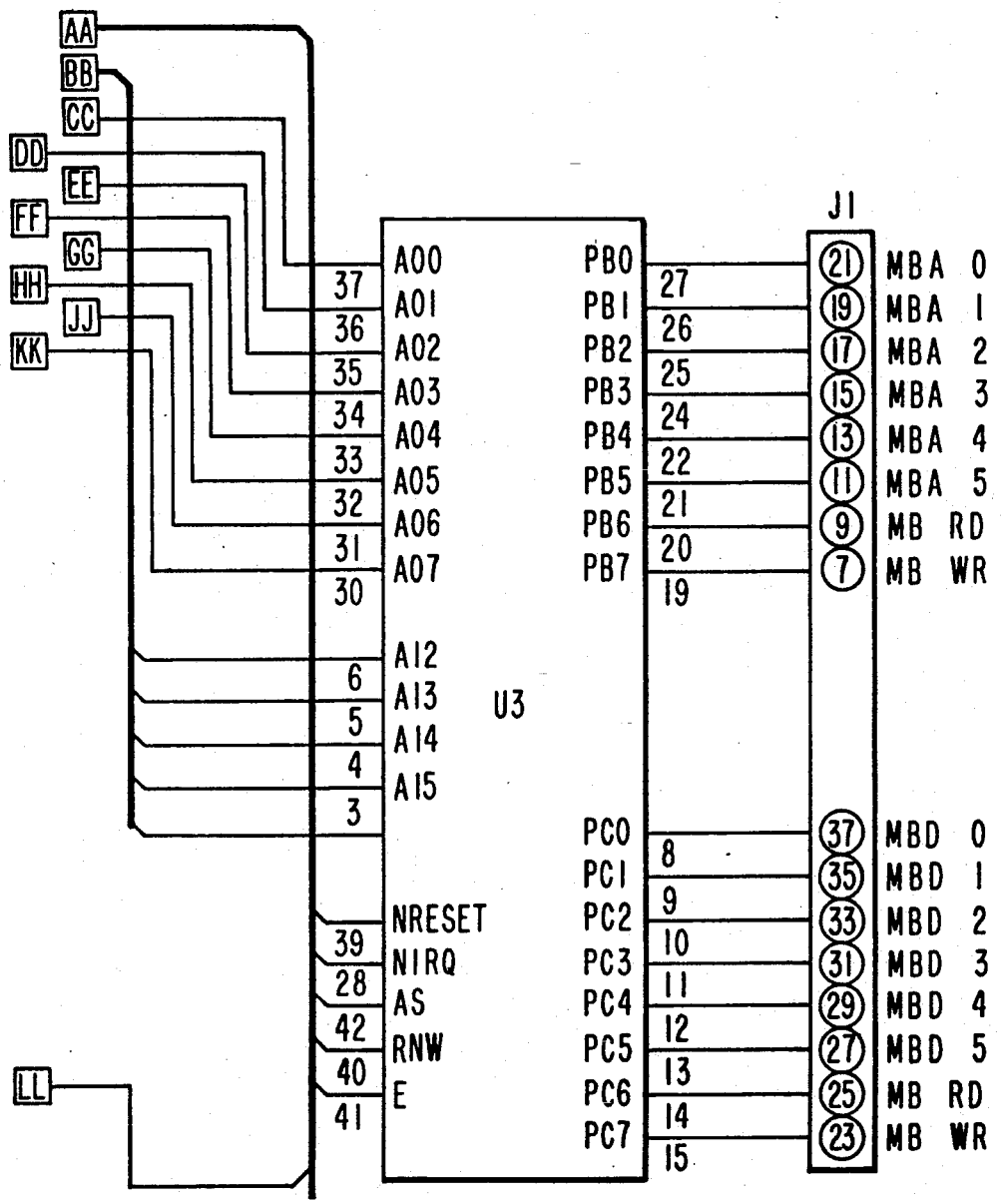
Figure 17:
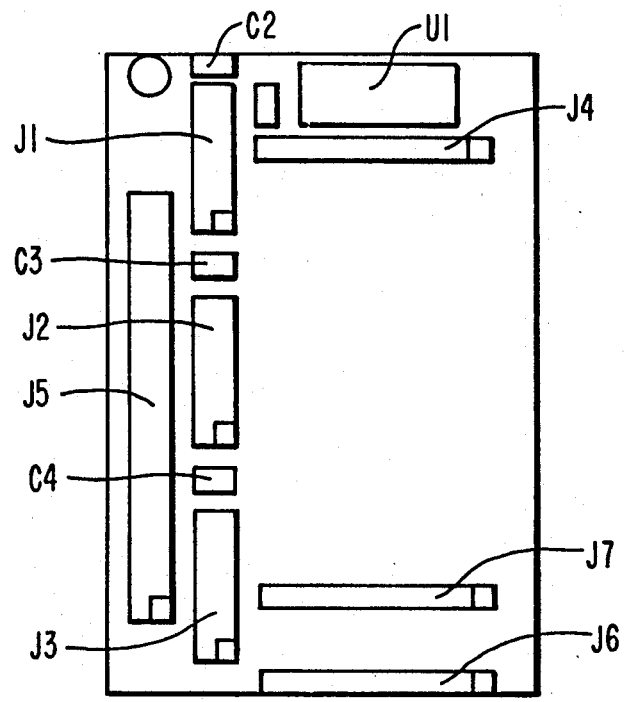
FIGS. 17 and 17A depict the placement of components on the local controller circuit board and local controller interface circuit board.
Figure 17A:
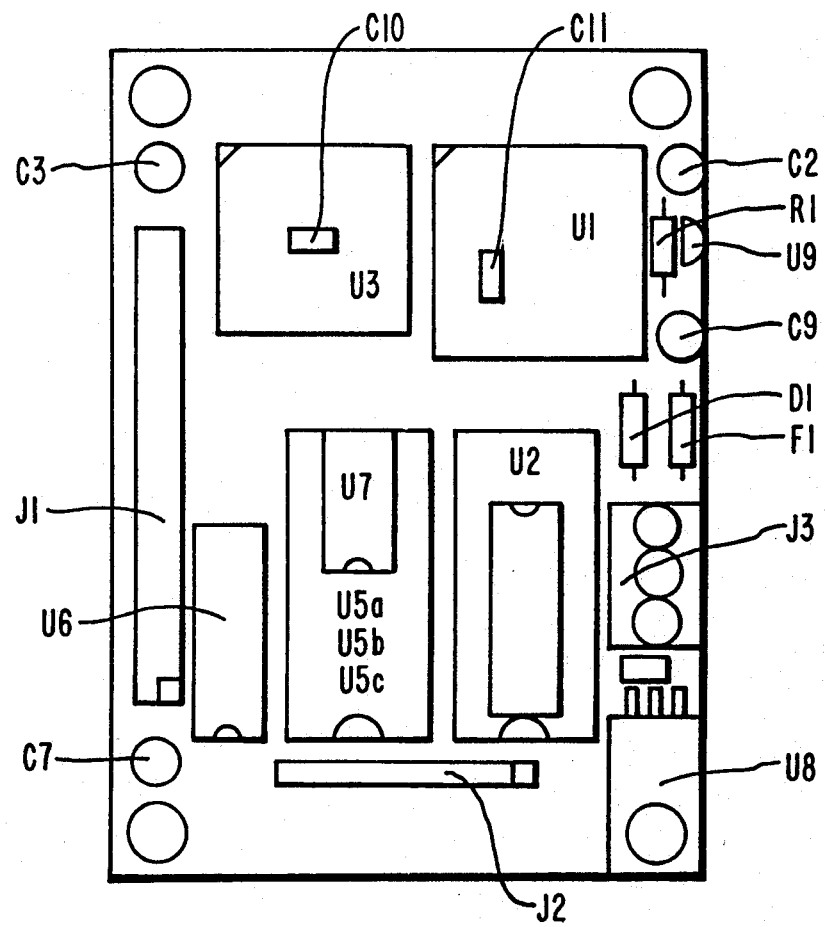
Figure 18:
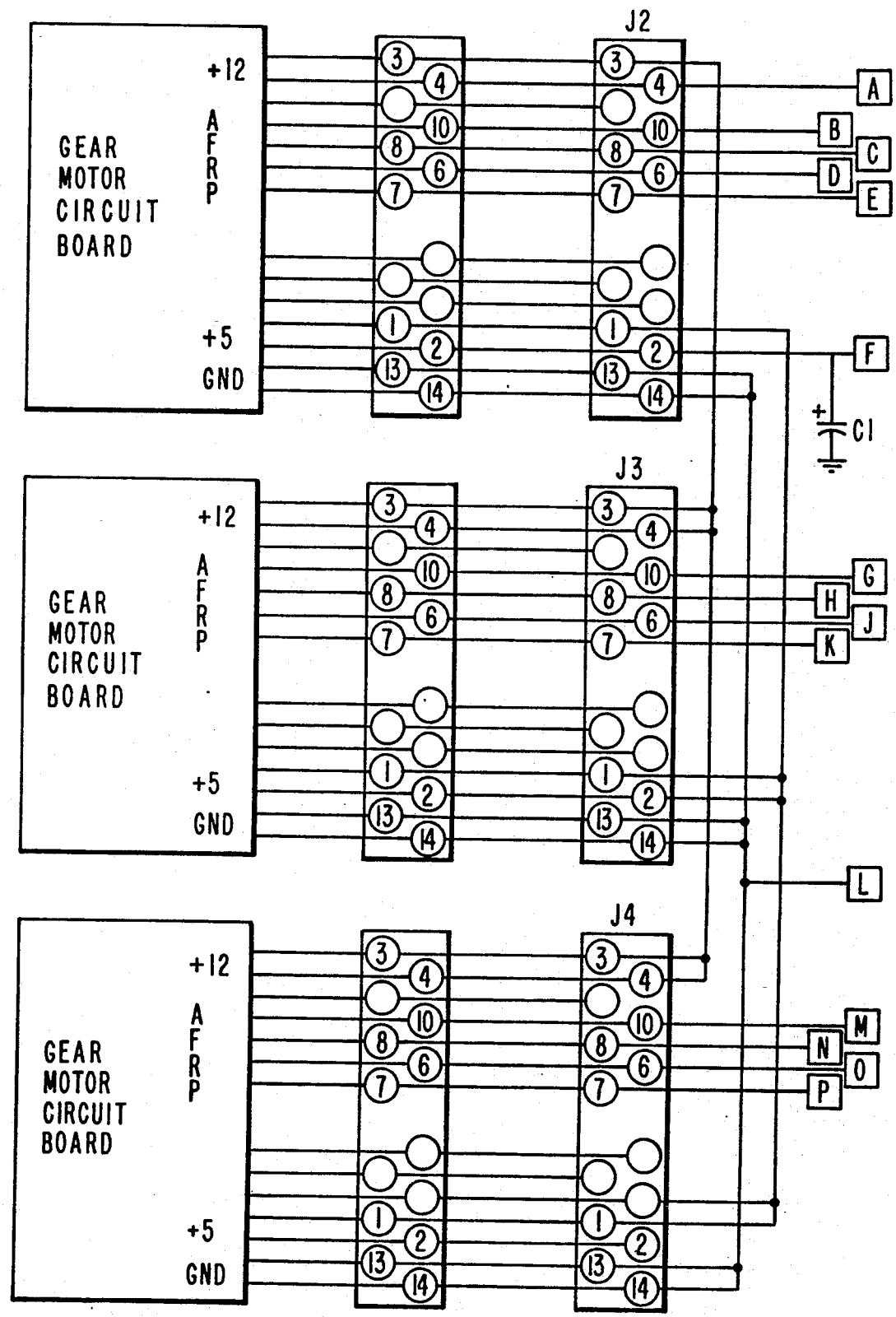
FIGS. 18 and 18A depict the electrical schematic of a local controller interface.
Figure 18A:
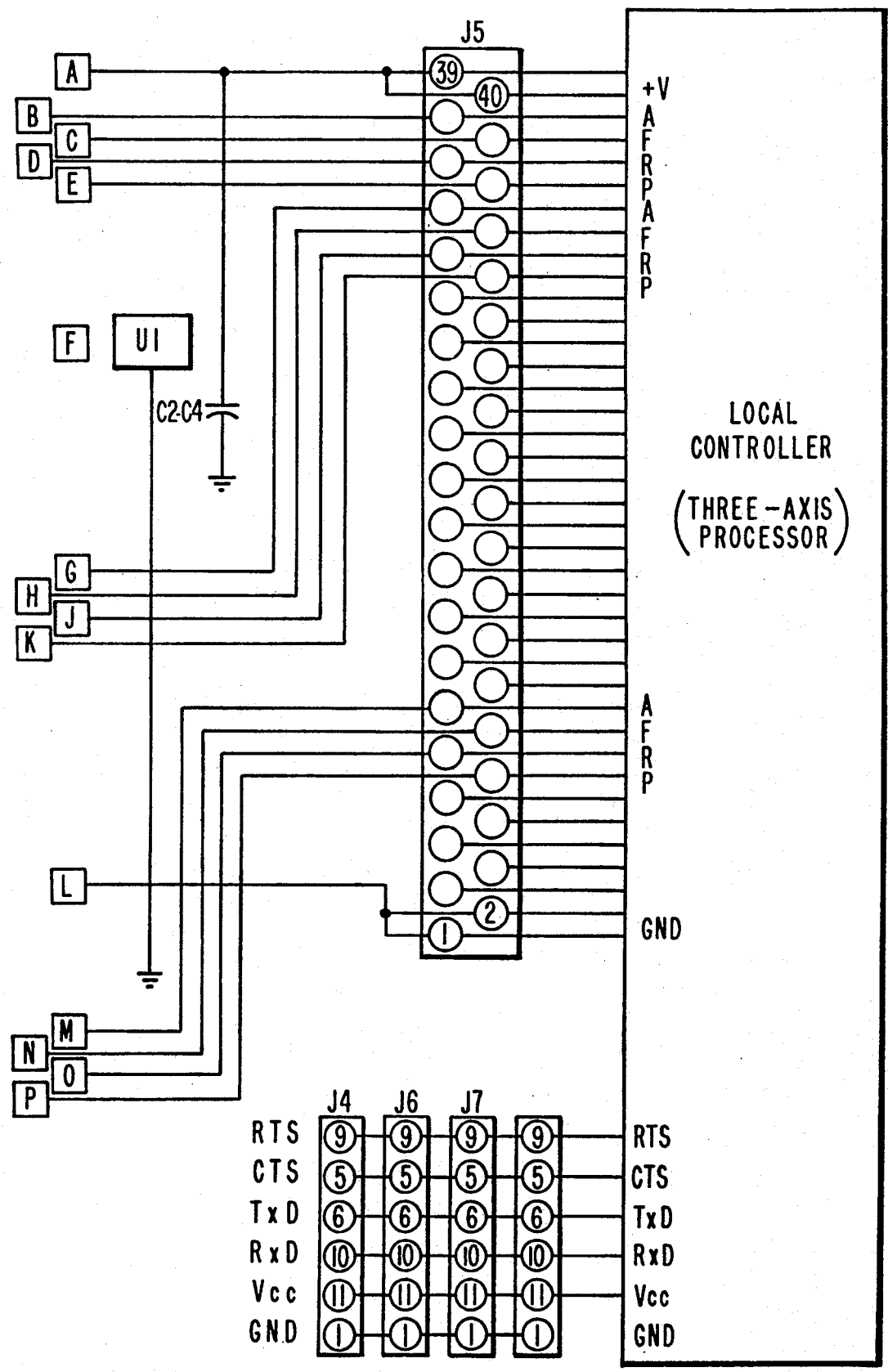

FIG. 16 depicts an electrical schematic of the local controller circuitry. FIG. 18 depicts an electrical schematic of the local controller interface circuitry. FIG. 17 shows the placement of components on the local controller circuit board and on the local controller interface circuit board. A list and description of the local controller and local controller interface components are set forth in Table 2 below:

TABLE 2

Component List - FIGS. 16, 17 and 18
Local Controller and Local Controller Interface

| Location | Manufacturer P.N. Manufacturer | Description |
|---|---|---|
| BD1 | PCB-0032B-01 parvus | Multi-purpose parvNET Node pcb |
| C1 | AS303A20 Rogers | 20 pin flat capacitor, .03 ufd |
| C11 | C320C104K5R5CA Kemet | Ceramic dipped 100 v capacitor .1 ufd |
| C2 | PDT6.8/50K Panasonic | 6.8 ufd 50 v capacitor |
| C3 | 513D686M016AA4 Sprague | 68 ufd 16 v tantilum cap, .1 lead spacing |
| C7 | TB47/6.3V | 47 ufd, 6.3 v tantalum capacitor |
| C8 | C320C104K5R5CA Kemet | Ceramic dipped 100 v capacitor .1 ufd |
| C9 | TB47/6.3V | 47 ufd, 6.3 v tantalum capacitor |
| D1 | 1N4005 Motorola | 1 amp rectifier, 100 piv |
| J1 | 929647-01-20-10 Dupont | dual 10th in grid male connector - 20 pos |
| J2 | 929647-01-11-10 3M | sgl row .10" ml header, .235 above plastic, gold, 11 pos |
| J3 | KRE3 Lumberg | 3 position Lumberg terminal |
| R1 | R25J103 Rohm | 10k resistor, ¼ watt, 5% film |
| U1 | MC68HC11A1FN Motorola | CMOS processor |
| U1 | 821551-1 Amp | 52 pin quad pack socket |
| U2 | MC74HC573N Motorola | tri-state octal d-type latch |
| U3 | XC68HC24PN Motorola | Port replacement unit |
| U3 | 821575-1 Amp | 44 pin quad pack socket |
| U4 | NMC27C256Q20 National | 32k × 8 CMOS EPROM 200NS |
| U4 | 1CT-286-S-TG Robinson/Nug | 28-pin machined low profile socket |
| U5 | 1CT-286-S-TG Robinson/Nug | 28-pin machined low profile socket |
| U5A | M5M5256P-12L Mitsubishi | 32K × 8 static RAM |
| U6 | D5C031-40 Intel | 20 pin EPLD |
| U7 | MTOT1537.3728MHZ M-Tron | 7.3728 MHz Crystal |
| U8 | 7805CT Motorola | 5 vdc regulator, TO-220 case |
| U9 | S8054HN Seiko | low voltage indicator |
| BD1 | PCB-0033A-01 parvus | Three-axis interface printed circuit borad |
| C1 | TB47/6.3V | 47 ufd, 6.3 v tantalum capacitor |
| C2-C4 | C320C104K5R5CA Kemet | Ceramic dipped 100 v capacitor .1 ufd |
| J1-J3 | 68021172 Dupont | Berg Stic 11 header -rt angle double row |
| J4 | 68016-1-11 Dupont | sng row rt agl male header .10" grid 11 × 1 pos |
| J5 | 929852-01-20-10 Dupont | dbl row fem header, .10" grid 20 × 2 pos |
| J6 pos | 929850-01-11-10 3M | single row fem header, .10" grid, gold plate, 11 |
| U1 | 7805CT Motorola | 5 vdc regulator, TO-220 case |

Figure 6:
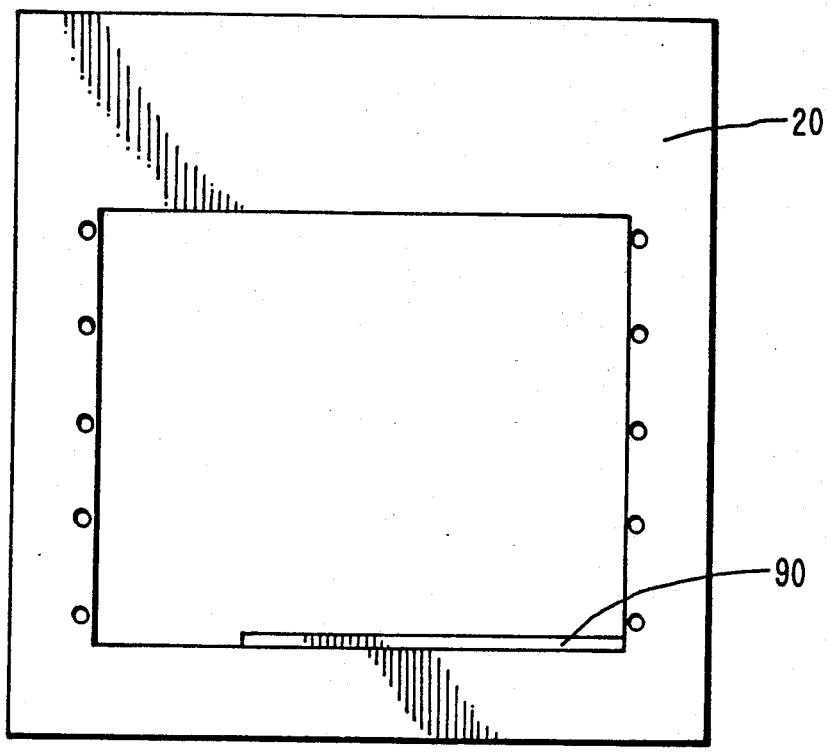
FIGS. 6, 6A, and 6B depict positions of the battery used as a local power source and infra-red transceiver positioning.
Figure 6A:
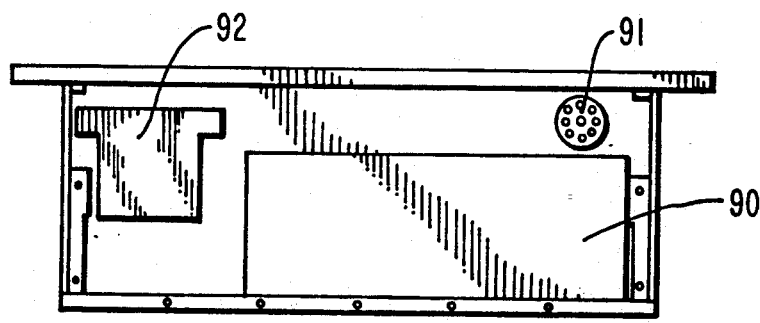
Figure 6B:
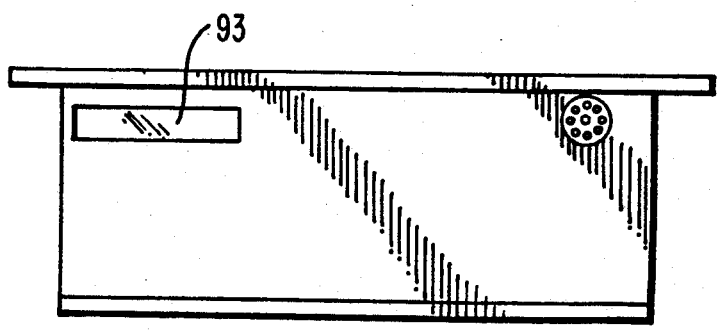
Figure 7:
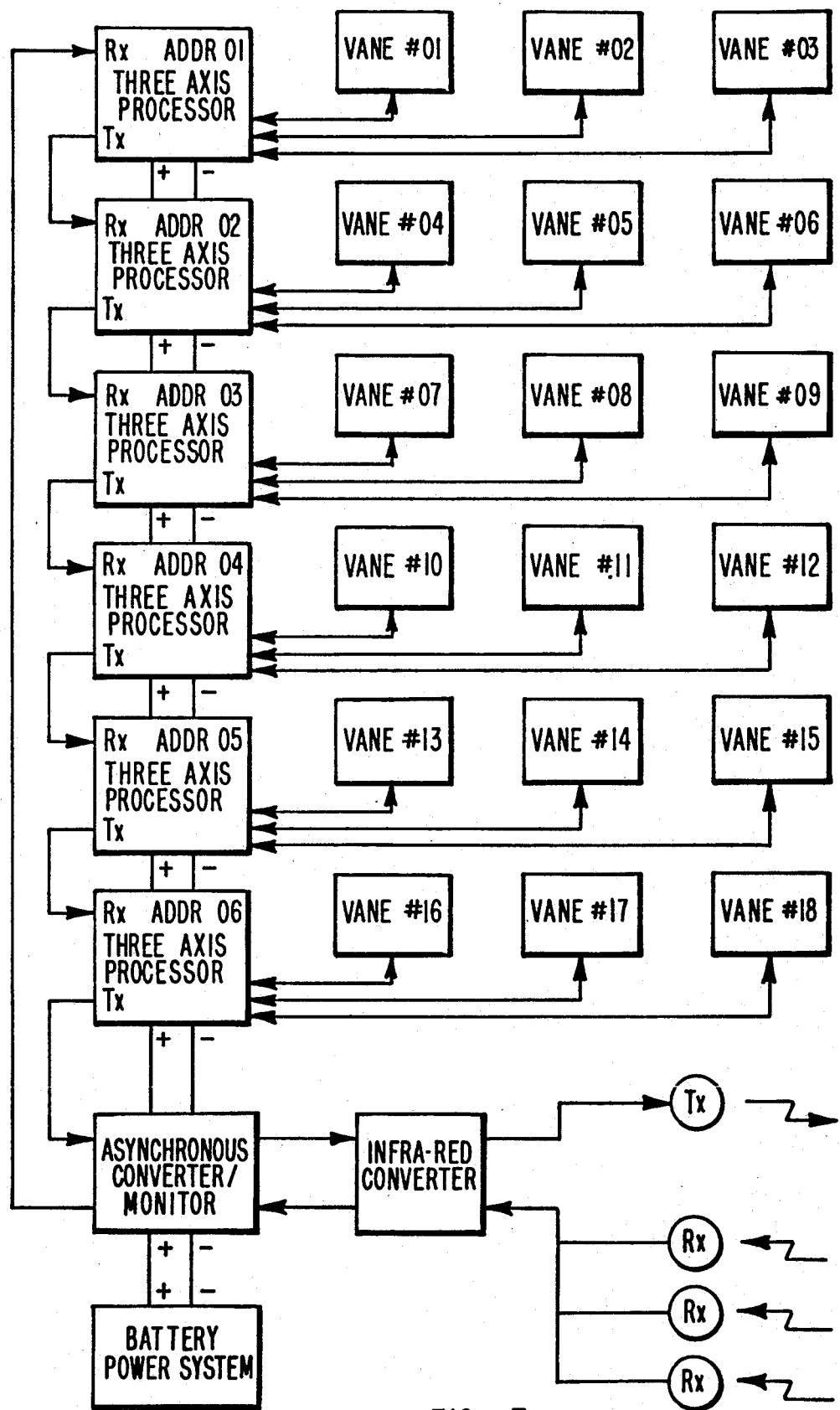
FIG. 7 depicts an Electron Aperture Block Diagram.

The local controllers, the infra-red transceiver and the vane movement means (e.g. gear motor) are powered by a local power source positioned within the collimator housing. In this embodiment of the invention, the local power source is a 12 v 1.9 amp battery (GS Portalac). View of Battery Power Location and Infra-red Transceiver Location is depicted in FIG. 6. Battery power system attachment is depicted in FIG. 7. The concept of a local power source (e.g. battery) in a portable electron beam collimator is one of the innovations of our invention. The dynamic multivane electron arc beam collimator is used on an intermittent basis for electron arc therapy. Its entire powered use cycle will typically be short (less than 15 minutes in many cases). The collimator can be removed from the linear accelerator and from the treatment room when not in use. During the periods of nonuse, the battery in the collimator can be charged by a battery charger through the battery charger port 39 (see FIG. 2). The local power source (e.g. battery) need only sustain the collimator for short periods of time such as one to two hours. High current usage occurs during transient vane movement. The concept of a local power source within the portable collimator eliminates the need for extra wiring and connections to the linear accelerator. The collimator is powered independent of the linear accelerator or any connection to the linear accelerator.

Figure 19A:
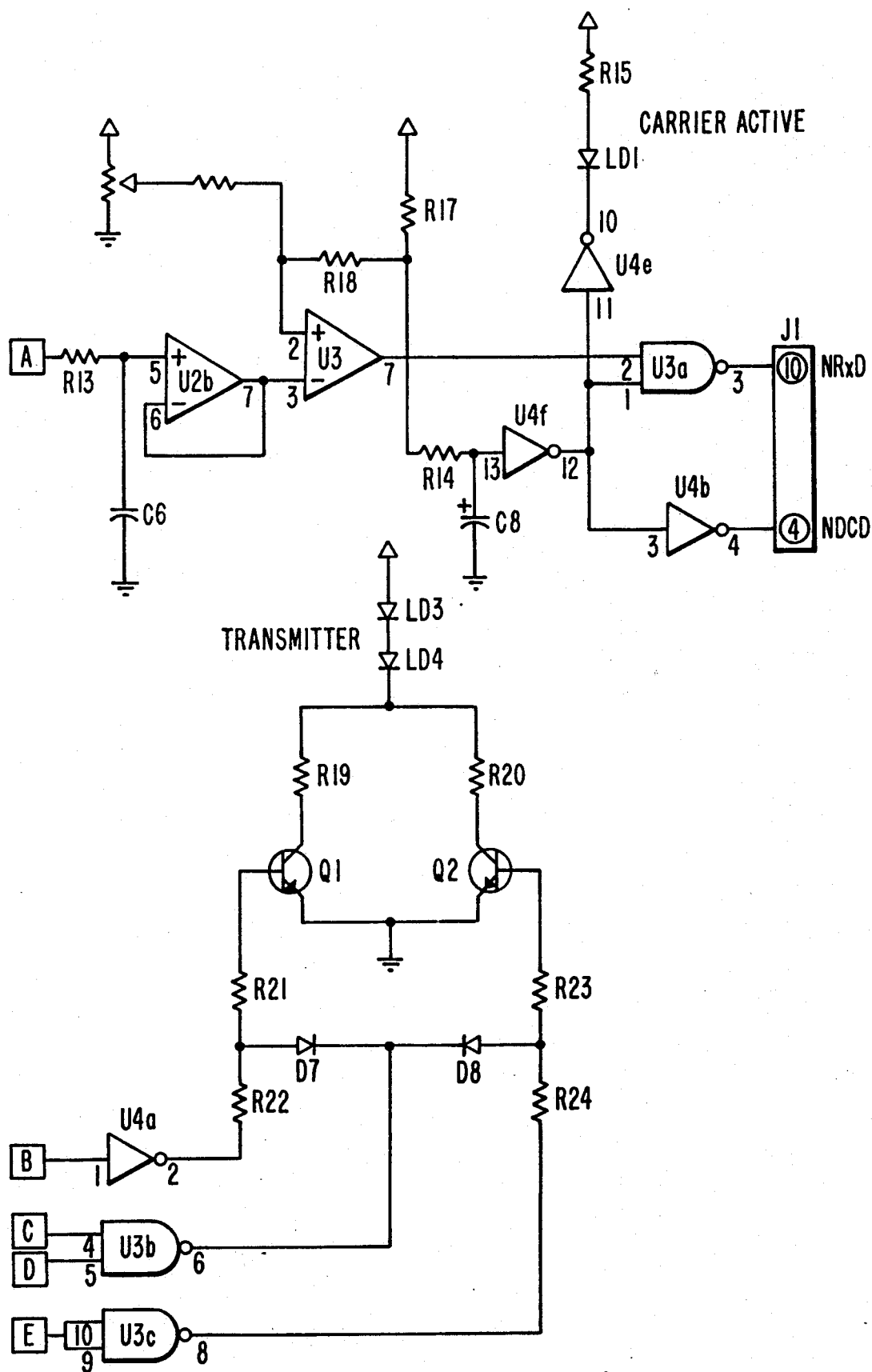
Figure 20:
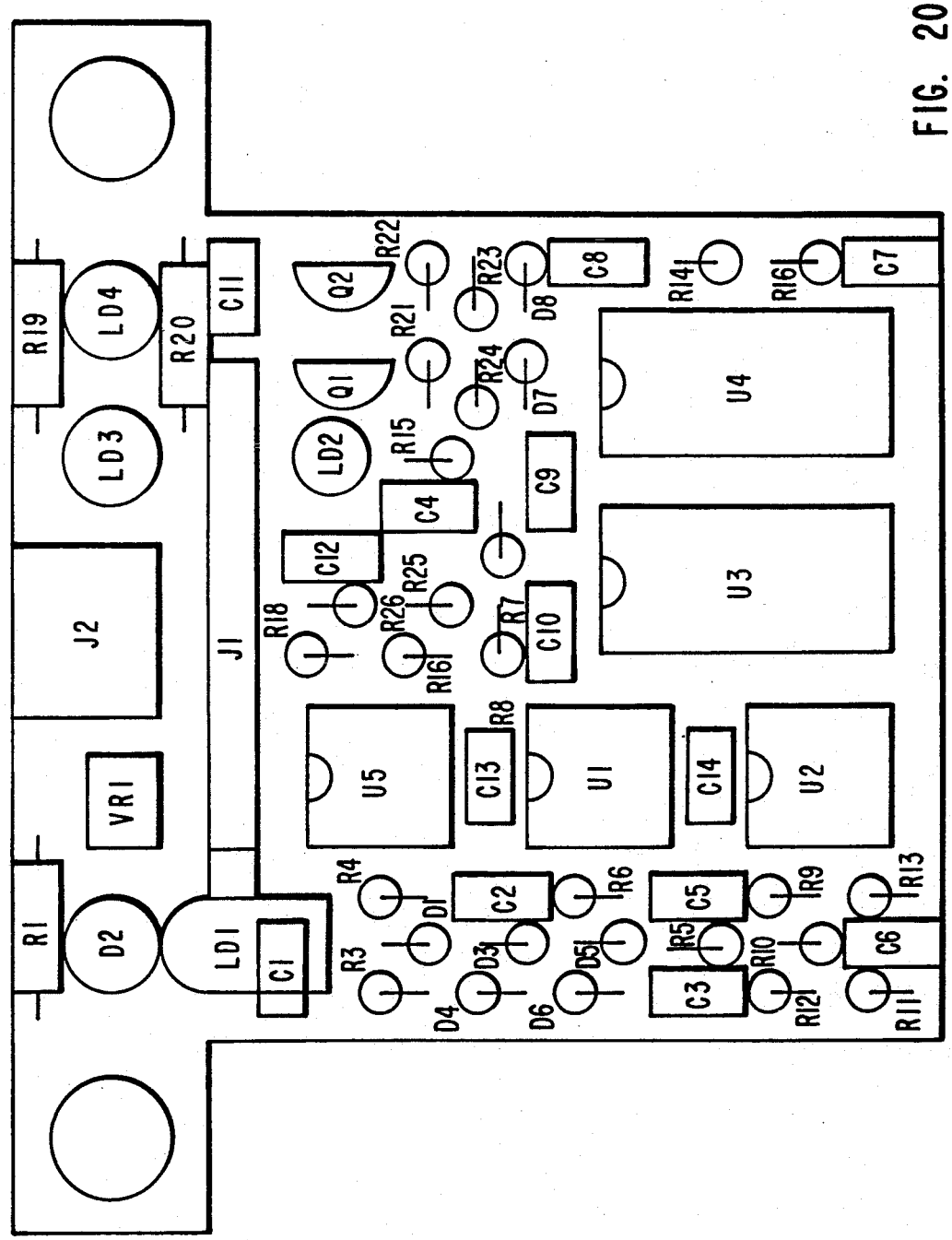
FIG. 20 depicts the placement of components on the infra-red transceiver circuit board.

FIG. 1 depicts infra-red transceivers 6a and 6b. Transceiver 6a is positioned within the housing of collimator 5. Transceiver 6b is positioned on wall 14 within the radiation treatment room. The infra-red transceivers provide for noncontact communication between collimator 5 and host controller 12. Noncontact communication means the communications from one device to another without physical electrical connections. FIG. 19 depicts an electrical schematic of the circuitry of infra-red transceivers 6a and 6b. FIG. 20 shows the placement of components on the infra-red transceiver circuit boards. A list and description of infra-red transceiver components are set forth in Table 3 below:

| Location | Component List - FIGS. 19 and 20 Infra-red Transceiver Manufacturer P.N. Manufacturer | Description |
|---|---|---|
| BD1 | PCB-0054B-01 parvus | Infra-red printed circuit board |
| C1 | T350E685M025AS Kemet | 6.8 ufd 25 v capacitor |
| C10 | C320C104K5R5CA Kemet | Ceramic dipped 100 v capacitor .1 ufd |
| C11 | C320C104K5R5CA Kemet | Ceramic dipped 100 v capacitor .1 ufd |
| C12 | C320C104K5R5CA Kemet | Ceramic dipped 100 v capacitor .1 ufd |
| C13 | C320C104K5R5CA Kemet | Ceramic dipped 100 v capacitor .1 ufd |
| C14 | C320C104K5R5CA Kemet | Ceramic dipped 100 v capacitor .1 ufd |
| C2 | C320C104K5R5CA Kemet | Ceramic dipped 100 v capacitor .1 ufd |
| C3 | CW15C103M Centralab | Ceramic dipped 100 v capacitor .01 ufd, 20% tolerance |
| C4 | C320C104K5R5CA Kemet | Ceramic dipped 100 v capacitor .1 ufd |
| C5 | C315C221K2G5CA Kemet | 220 pfd 200 v ceramic capacitor, +/−10% |
| C6 | CY15C222M CentraLab | .002 ufd ceramic dipped capacitor |
| C7 | C320C102K5R5CA Kemet | .001 ufd ceramic capacitor |
| C8 | T350E685M025AS Kemet | 6.8 ufd 25 v capacitor |
| C9 | C320C104K5R5CA Kemet | Ceramic dipped 100 v capacitor .1 ufd |
| D2 | SDP8403-301 Honeywell | Infra-red phototransistor |
| D3 | 1N914 SEM | small signal diode-fast recovery |
| D4 | 1N914 SEM | small signal diode-fast recovery |
| D5 | 1N914 SEM | small signal diode-fast recovery |
| D6 | 1N914 SEM | small signal diode-fast recovery |
| D6 | 1N914 SEM | small signal diode-fast recovery |
| D8 | 1N914 SEM | small signal diode-fast recovery |
| J1 | 929850-01-11-10 3M | shs row fom 1 dr, .10" grid 11 × 1 pos |
| LD2 | SLR34UR# Rohm | LED, Rad ⅛" dia. |
| LD3 | SEP8703-001 Honeywell | high output infra-red LED, clear |
| LD4 | SEP8703-001 Honeywell | high output infra-red LED, clear |
| Q1 | 2N4400 Motorola | general purpose NPN |
| Q2 | 2N4400 Motorola | general purpose NPN |
| R1 | R25J102 Rohm | 1k ohm, ¼ watt, 5%, film |
| R10 | R25J103 Rohm | 18k resistor, ¼ watt resistor, 5%, film |
| R11 | RN55DS103F Dale | 510K ¼ watt resistor, 5%, film |
| R12 | R25J103 Rohm | 10k resistor, ¼ watt, 5%, film |
| R13 | | 2.2k ohm, 5%, film |
| | Rohm | |
| R14 | R25J333 Rohm | 33K ¼ watt resistor, 5%, film |
| R15 | R25J470 Rohm | 470 ohm resistor, ¼ watt, 5%, film |
| R16 | R25J102 Rohm | 1k ohm, ¼ watt, 5%, film |
| R17 | R25J102 Rohm | 1k ohm, ¼ watt, 5%, film |
| R18 | R25J104 Rohm | 100k, ¼ watt, 5%, film |
| R19 | R25J511 Rohm | 510 ohm, ¼ watt resistor |
| R2 | R25J273 Rohm | 27K ¼ watt resistor, 5%, film |
| R20 | R32GF100J Resistors | 10 ohm 1 watt resistor |
| R21 | R25J102 Rohm | 1k ohm, ¼ watt, 5%, film |
| R22 | R25J102 Rohm | 1k ohm, ¼ watt, 5%, film |
| R23 | R25J102 Rohm | 1k ohm, ¼ watt, 5%, film |
| R24 | R25J102 Rohm | 1k ohm, ¼ watt, 5%, film |
| R25 | R25J103 Rohm | 10k resistor, ¼ watt, 5%, film |
| R26 | R25J101 Rohm | 100 ohm, ¼ watt, 5%, film |
| R3 | Rohm | 2.2k ohm, 5%, film |
| R4 | R25J104 Rohm | 100k, ¼ watt, 5%, film |
| R5 | R25J221 Rohm | 220 ohm ¼ watt resistor, 5%, film |
| R6 | CRB14FX2002 Rohm | 28k, ¼ watt resistor, metal oxide fixed |
| R7 | R25J221 Rohm | 220 ohm ¼ watt resistor, 5%, film |
| R8 | R25J105 Rohm | 1 meg ohm, ¼ watt, 5%, film |
| U1 | TDA2320 S6S | Infra-red pro-amp |
| U2 | LM358N Motorola | LIN - dual op amp |

-continued

| | Component List - FIGS. 19 and 20 Infra-red Transceiver | |
|---|---|---|
| Location | Manufacturer P.N. Manufacturer | Description |
| U3 | MC74HC00N Motorola | quad 2-1 NAND gate |
| U4 | M74HC14B1 S6S-ATES | hex schmitt trigger |
| U5 | LM311N Motorola | General purpose comparator |
| VR1 | VRN182-20K Vernitron | 20k potentiometer |

Figure 11:
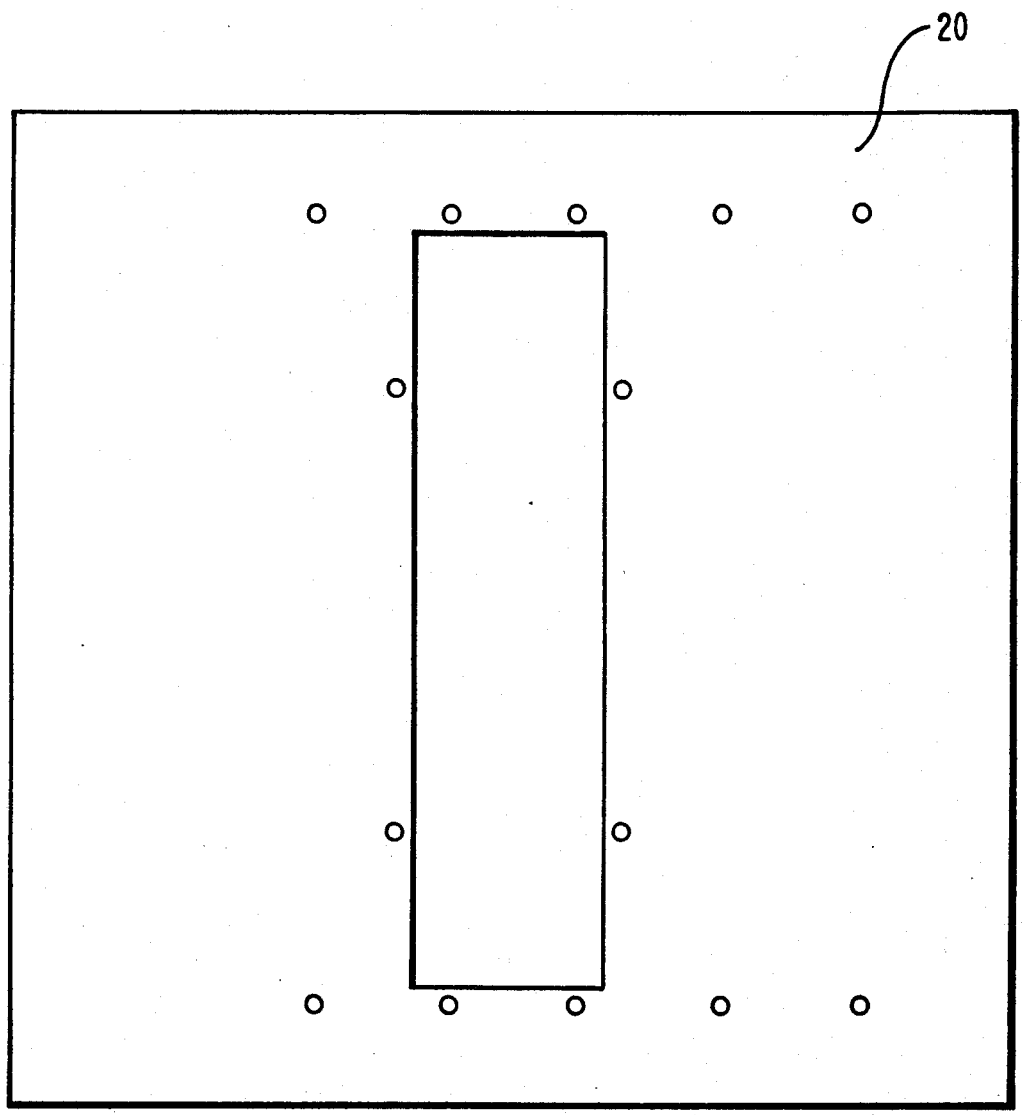
FIG. 11 depicts the bottom plate of the housing as a clinical use plate.

The vanes, the vane movement means, the local controllers (including interfaces), the infra-red transceiver 6a and the local power source (e.g. battery) are contained within a housing. The housing of this invention can be a housing, chassis or support for three other collimator elements. The housing is constructed of plates as shown in FIG. 10. The plates are bolted together to form the housing which can also be seen in FIG. 2. In FIG. 10 the Bottom View shows the bottom plate as a maintenance plate. The maintenance plate has a large opening to facilitate access to the vanes, vane movement means and controllers. In actual electron arc therapy use a clinical use bottom plate having a smaller opening should be used. A clinical use bottom plate is depicted in FIG. 11. Referring again to FIG. 10, the Top View depicts the top plate of the collimator housing. The Side View depicts the side plates of the collimator housing. FIG. 10 also includes a Front View and a Back View where a front plate (not shown) and a back plate (not shown) should be positioned and bolted to the side brackets described below. The Front View shows use of two side brackets to secure the side plates to the top plate. The Back View shows nine vane assemblies. The concept of including the vanes, vane movement means, local controllers, noncontact communications means (e.g. infra-red transceiver) and local power source within a portable collimator housing represents one of the innovations of our invention. This housing innovation facilitates the use and installation of the collimator.

Computer 12 (see FIG. 1) functions as the host controller of the collimator 5. The host controller can be an IBM PS/2 Model 80 microcomputer, a microVAX II minicomputer or some other kind of computer. The host controller 12 executes a computer program which we have named the "Collimator Treatment Conversion Program" or "Conversion Program." The Conversion Program was programmed in the Fortran programming language. A source code listing of the Conversion Program is filed with, and as part of, this patent application and is incorporated by reference into this specification. The Conversion Program converts a graphical image of the target area (or treatment area) of the patient into nine dosage planes (which correspond to the nine vane pairs in this embodiment of the invention). These dosage planes are parallel to the gantry rotational plane of the linear accelerator. For purposes of rotational reference, the arc of rotation is defined by 360 degrees of rotation with the point directly below the isocenter designated as zero degrees.

Because the linear accelerator head does not typically rotate the full 360° around the patient, only a selected treatment arc (which is a subset of a full 360 degree rotation) is used and only the arc segments (described below) within the selected treatment arc are used. Typically, the selected treatment arc will represent a rotational arc of about 90 to 270 degrees. Our invention is not, however, limited to this typical range of operation. Only the vane pair openings and vane position data calculated for arc segments within the selected arc (or treatment arc) are needed and retained for use.

The following process is conducted sequentially for each vane pair (i.e. for each dosage plane):

1. The selected treatment arc is divided by the user into a plurality of arc segments. Arc segments are defined by the user by defining or selecting reference angles. In this embodiment the reference angles are selected at every five degrees of rotation. Other reference angles can be used.
2. The user selects reference points which are points located within the patient, preferably equally spaced across the treatment arc, at a depth below the patient surface corresponding to the depth of dose maximum of the electron beam.
3. For the first arc segment, the Conversion Program calculates the dosage quantity for each reference point within the dosage plane for each possible width of the opening defined by the vane pair. Possible widths are defined incrementally (e.g. in 1 millimeter increments) and range from minimum opening to maximum opening.
4. Step 3 is repeated for each of the remaining arc segments.
5. The Conversion Program uses a least squares optimization algorithm to determine a single preferred vane pair opening for each arc segment which provides the most uniform dose distribution across the entire treatment arc. For example, if the treatment arc is divided into ten arc segments then the vane pair will have ten openings assigned to it, one for each of the ten arc segments.

Steps 1 to 5 are repeated for each of the remaining vane pairs (i.e. dosage planes). For nine vane pairs the process is conducted nine times, once for each vane pair. For nine vane pairs and ten arc segments the end result is a data file of 90 preferred vane openings. Each vane pair opening is independent of the other vane pair openings. The preferred vane pair openings are defined by vane position and are represented by vane position data. This data file (i.e. the vane position data) is transported to the host controller 12. This data file is referred to as the vane position data file. The vane position data file is indexed by reference angle.

The vane pair openings calculated by the Conversion Program are indexed by reference angle for each dosage plane. The electron arc dose calculations used in the Conversion Program explicitly account for changes in patient shape across the arc, changes in patient density within the treatment volume, and changes in dose rate and energy across the arc. The preferred vane pair openings are converted to data representative of vane positions which will define the electron aperture needed to provide the desired uniform electron dosage. The vane position data are stored sequentially in a data file for later transmission to the collimator at the appropriate times (i.e. at appropriate reference angles) during the rotation of the linear accelerator head and collimator through the selected treatment arc. The data file for the complete treatment is preferably calculated before rotation begins.

The invention is not limited to the specific Conversion Program or settings described herein. Other computer programs can be developed to serve as the Conversion Program or described settings. Changes within the scope of our invention can be made to the Conversion Program. For example, the reference angles can be different than every five degrees of rotation. The Conversion Program in combination with the necessary computer hardware and user input represents a means for creating vane position data (the "vane position data creation means"). This also represents a means for determining preferred vane pair openings for each arc segment and for representing the preferred vane pair openings as vane position data for each arc segment.

The data file containing the vane position data is indexed by reference angles. The data file contains a record of vane position data for each reference angle. [Note: Each reference angle identifies the arc segment which begins with the reference angle. (Two reference angles, a beginning reference angle and an ending reference angle, define an arc segment. The beginning angle, as determined by rotational direction, is the identifying reference angle. The ending reference angle will be the beginning or identifying reference angle for the next arc segment (if there is a next arc segment)]. Each such record contains data representing the desired position of each of the eighteen vanes for the reference angle and the arc segment identified by the reference angle. As the linear accelerator head and collimator rotate through the selected treatment arc, the vanes will be moved to their appropriate positions for each record, i.e. as each new reference angle is encountered the vanes will be moved to the positions that will define the electron aperture needed to provide the desired electron dosage corresponding to the arc segment. When the next reference angle is encountered the vanes will be moved to new positions to define the next electron aperture needed to provide the desired electron dosage corresponding to the next arc segment.

Computer 11, the controller of the linear accelerator 1, monitors the treatment angle of the linear accelerator as the head 3 and collimator 5 rotate through the selected treatment arc. Computer 11 provides this treatment angle data to host controller 12 (i.e. computer 12) by transmitting an RS-232 asynchronous serial signal through cable 16 to a standard asynchronous serial port of host controller 12 (see FIG. 1).

Host controller 12 executes a computer program which we have named the "Remote Collimator Control Program" or "Control Program". The Control Program was programmed in the Basic programming language (QuickBasic 4.0). A source code listing of the Control Program is filed with, and as part of, this patent application and is incorporated by reference into this specification. The Control Program monitors the treatment angle data received from computer 11 via cable 16. In this manner the host controller 12 is kept informed of the current treatment angle and can detect reference angles which are encountered by linear accelerator rotation. For each treatment angle that is a reference angle, the Control Program converts the vane position data corresponding to the arc segment identified by the reference angle into error checked communications packets (one packet for each local controller) and sends the communications packets (i.e. the vane position data) to collimator 5 via cable 17 and infra-red transceiver 6b. The Control Program appends a CRC value to the packet based upon the data values of the packet.

The invention is not limited to the specific Control Program. Other computer programs can be developed to serve as the Control Program. Changes within the scope of our invention can be made to the Control Program. The Control Program in combination with the necessary hardware represents a means for monitoring the treatment angle of the linear accelerator rotation (i.e. during rotation of head 3 and collimator 5 along the arc of rotation or treatment arc) to detect reference angles when encountered by such rotation and for transmitting to the collimator vane position data for each reference angles encountered during linear accelerator rotation (the "vane position data transmission means"). The vane position data for a reference angle is the vane position data for the arc segment identified by the reference angle.

Figure 5:
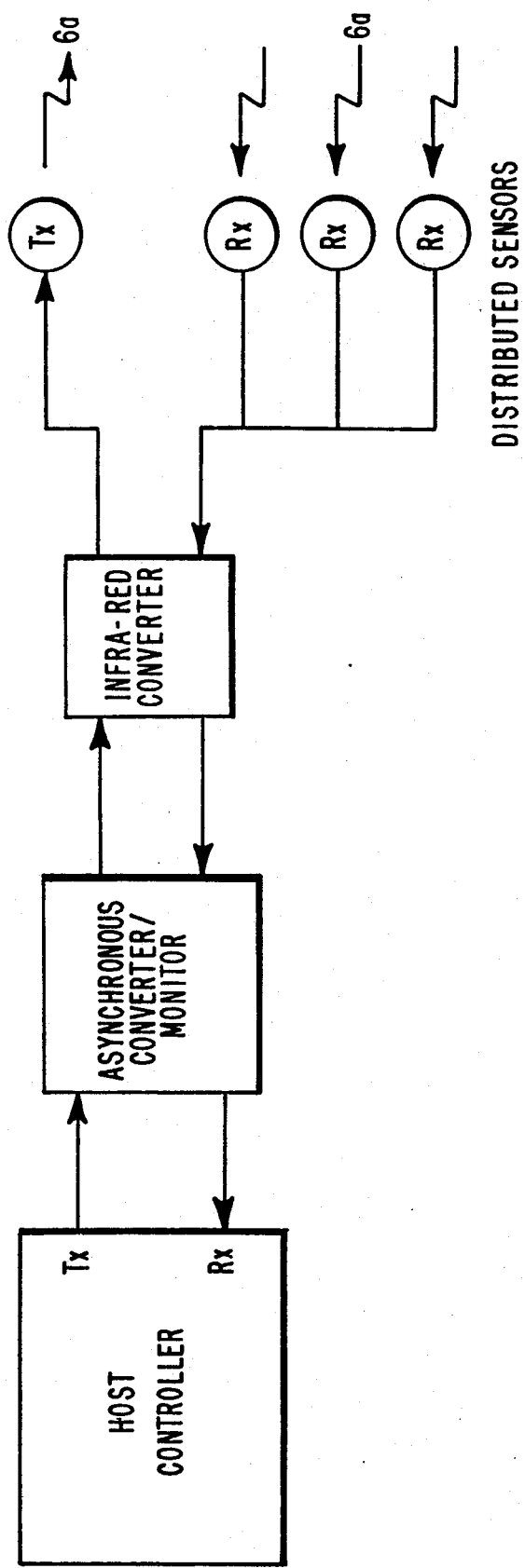
FIG. 5 depicts an electron aperture controller.

The communications packets (i.e. vane position data) for the reference angle (and corresponding arc segment) are transmitted by infra-red transceiver 6b to infra-red transceiver 6a in collimator 5. Each communications packet is sent by host controller 12 to transceiver 6b in the form of an RS-232 asynchronous serial signal through cable 17 (see FIG. 1). The infra-red transceiver 6b includes an asynchronous converter/monitor and an infra-red converter (see FIG. 5). The asynchronous converter/monitor converts the RS-232 signal into a 0-5 v TTL signal (transistor/transistor logic signal). The infra-red converter converts the TTL signal into an infra-red signal for noncontact transmission to the infra-red transceiver 6a in collimator 5. Infra-red transceivers 6a and 6b are capable of transmitting infra-red signals to each other and receiving infra-red signals from each other as indicated by arrows 18 in FIG. 1. Transceiver 6a also includes an asynchronous converter/monitor and an infra-red converter as depicted in FIG. 7. In this manner noncontact transmission and reception can be conducted. Each infra-red transceiver includes distributed sensors to receive infra red transmissions from the other transceiver. Although only one infra-red transceiver 6b is shown in FIG. 1, a plurality of infra-red transceivers 6b should be secured to wall 14 within the treatment room (i.e. the radiation therapy room) at different locations in position to transmit to and receive from transceiver 6a as it rotates along the selected treatment arc. The transceivers 6b can, in an alternative embodiment of the invention, be positioned in the plane defined by the selected treatment arc. This alternative would require that transceiver 6a be located on a different side of collimator 5 and that the transceivers 6b be located on a different wall (i.e. on one or both of the walls perpendicular to wall 14).

The infra-red signals (i.e. data packets) between transceiver 6a and 6b are amplitude modulated infra-red signals using a 100 khz carrier frequency. By using infra-red signals or some other noncontact form of communication (e.g., AM/FM radio frequency transmission) between host controller 12 and collimator 5, the need to add additional communication wiring to the rotating linear accelerator and collimator is eliminated.

Infra-red transceiver 6a converts the communications packets (i.e. vane position data) received from infra-red transceiver 6b through the infra-red converter and asynchronous converter/monitor of transceiver 6a and passes this vane position data to the local controllers (i.e. the six three-axis processors) as shown in FIG. 7. As each communication packet reaches its destination local controller, the local controller (i.e. three-axis processor) checks the integrity of the communications packet by calculating an incoming CRC value (cyclic redundancy check value) based on the data of the received packet and compares this value to the transmitted CRC value appended to the received packet. If the CRC comparison is valid, an acknowledgment packet is sent to the host controller 12 and the process of moving the vanes controlled by the local controller to their new positions begins. After all three vanes of a local controller have reached their new position an additional acknowledgment packet is sent to the host controller 12 for vane position verification.

Figure 9:
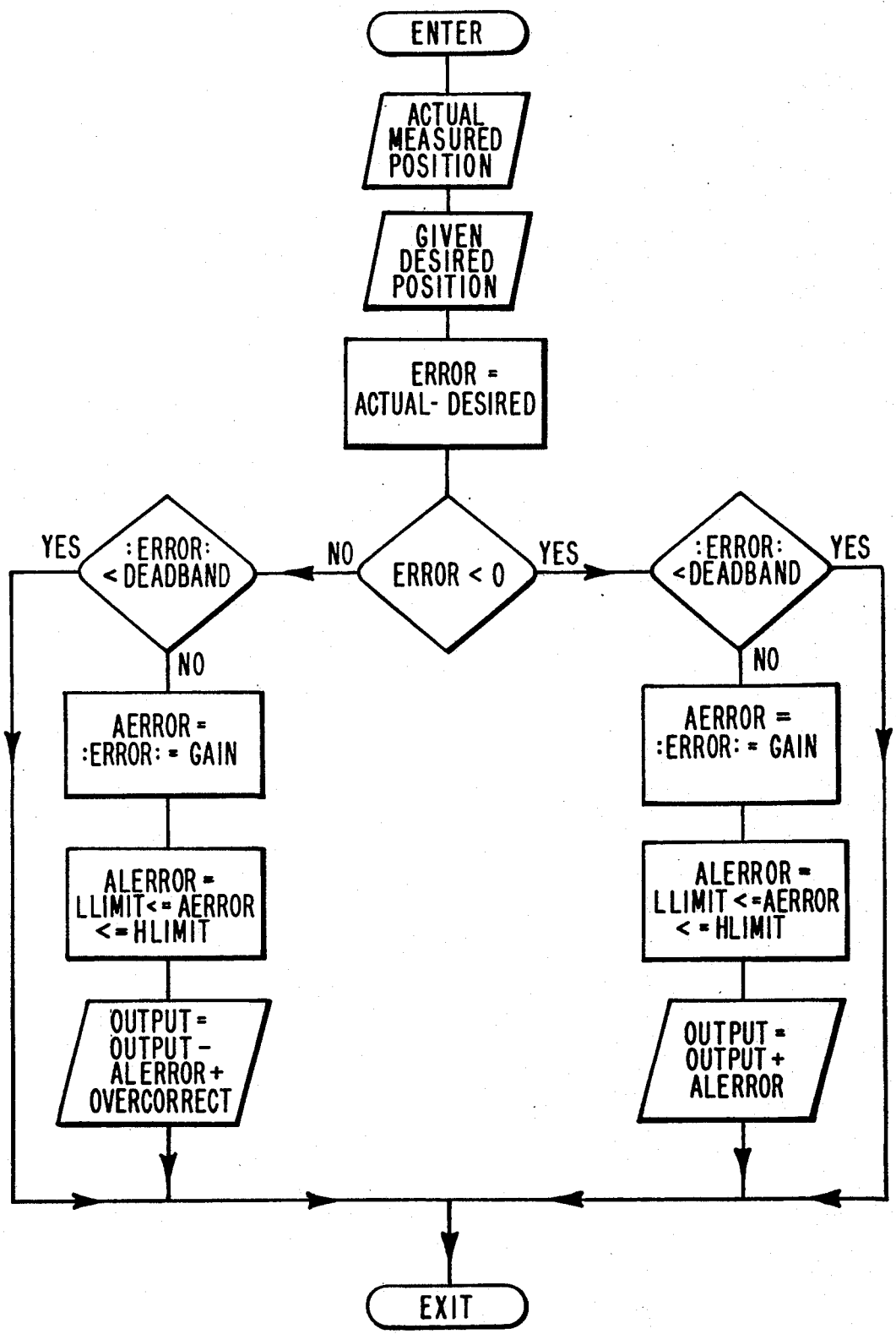
FIG. 9 depicts a Single Axis Control Loop.

Each local controller includes a computer program, the "Local Controller Program," embodied as firmware in the EPROM of the local controller. The Local Controller Program was programmed in Assembly language. A source code listing of the Local Controller Program is filed with, and as part of, this patent application and is incorporated by reference into this specification. The Local Controller Program provides negative feedback loop control for up to four simultaneous signals. FIG. 9 depicts a flow chart of a single axis loop. The Local Controller Program is a general purpose multiple axis control program. The parameters of the control loops of the Local Controller Program have been set to optimum values for the collimator hardware. These parameters are stored in permanent memory (EEPROM) of the local controller. The EEPROM embedded in the Local Controller is refreshed or rewritten on a periodic basis by the Local Controller Program to offset the gradual data retention degradation caused by exposure to elevated radiation levels. The Local Controller Program includes communication, monitoring and error detection systems. The Local Controller Program includes a time averaged 12-bit A/D (analog/digital) conversion routine to convert analog data from the position monitoring means (e.g. potentiometer) to 12 bit digital data. The output is a 12-bit PWM (pulse width modulated) signal derived from the system clock. Polarity is determined external to the PWM signal for additional resolution and control. Simple digital braking is provided for high inertial systems. Two inputs per channel allow for auto-calibration or position checking.

The six local controllers (i.e. the six three-axis processors) are located on a network. The parvNET token passing network of the parvus Corporation can be used for this purpose. As previously described the local controllers (three-axis processors) control and monitor the eighteen vanes (and the eighteen vane movement means corresponding to the vanes). See FIG. 7. The local controllers are networked as nodes on a common network. The host controller and display panel are also nodes on the network.

Commands are sent to each three-axis processor on the network at a speed 19200 baud with an average packet length of 13 bytes for a total 18 vane collimator access time of 40 ms per setting. Physical communications are sent using standard RS-232C signals and encoded infra-red pulses to allow minimum modification to Varian's 2100C.

There are parvNET registers in the Local Controller Program that are specifically defined for this application. They are defined only for this application and have no bearing on other applications. All unmentioned parvNET registers follow the standard definitions found in the parvNET PROTOCOL STANDARD (STD-0003x-01) of the parvus Corporation of Salt Lake City, Utah. The definitions of the registers specific to this application are given in Table 4 below.

TABLE 4

Register Definition

1. Register: 10
   Name: Desired Position
   Read: 8 total bytes
     Bytes
       0-1 - Desired Position Axis 1
       2-3 - Desired Position Axis 2
       4-5 - Desired Position Axis 3
       6-7 - Desired Position Axis 4
   Write: 8 total bytes
     Bytes
       0-1 - Desired Position Axis 1
       2-3 - Desired Position Axis 2
       4-5 - Desired Position Axis 3
       6-7 - Desired Position Axis 4
   Initialize: All bytes are set to zero as default.
     The on-board permanent memory is read,
     checksum verification is performed, and
     then if a proper checksum exists then
     all bytes are updated from the
     permanent memory values.
   The DESIRED POSITION register is the location in units
   that the negative feedback loop for the particular
   axis must try to achieve. The 12-bit right justified
   value stored for each axis can only be modified by the
   user.

2. Register: 20
   Name: Actual position
   Read: 8 total bytes
     Bytes
       0-1 - Actual Position Axis 1
       2-3 - Actual Position Axis 2
       4-5 - Actual Position Axis 3
       6-7 - Actual Position Axis 4
   Write: 8 total bytes
     Bytes
       0-1 - Actual Position Axis 1
       2-3 - Actual Position Axis 2
       4-5 - Actual Position Axis 3
       6-7 - Actual Position Axis 4
   Initialize: The A/D converters are read and entered
     into position calculations and stored
     in this register.
   The ACTUAL POSITION is the calculated 12-bit right
   justified value derived from the A/D converter
   connected to each axis. This value is compared to the
   DESIRED POSITION to determine the position error
   magnitude and polarity.

3. Register: 30
   Name: Raw A/D Values
   Read: 4 total bytes
     Bytes
       0 - Desired Position Axis 1
       1 - Desired Position Axis 2
       2 - Desired Position Axis 3
       3 - Desired Position Axis 4
   Write: None
   Initialize: The A/D converters are read and stored
     in this register
   The 8-bit values stored at these register locations
   are the actual values converted from the on-board A/D.

4. Register: 40
   Name: Deadband
   Read: 4 total bytes
     Bytes
       0 - Deadband for Axis 1
       1 - Deadband for Axis 2
       2 - Deadband for Axis 3
       3 - Deadband for Axis 4
   Write: 4 total bytes
     Bytes
       0 - Deadband for Axis 1
       1 - Deadband for Axis 2
       2 - Deadband for Axis 3
       3 - Deadband for Axis 4
   Initialize: All bytes are set to zero as default.
     The on-board permanent memory is read,
     checksum verification is performed, and
     then if a proper checksum exists then TABLE 4-continued Register Definition all bytes are updated from those
permanent memory values.
Any calculated error derived from the actual and
desired positions that is greater the deadband value
will cause an appropriate adjustment in the pwm output
value. If the error is less than the DEADBAND then
the output value is zeroed with the polarity set to
positive.

5. Register: 50
 Name: Maximum Velocity
 Read: 8 total bytes
  Bytes
   0-1 - Desired Position Axis 1
   2-3 - Desired Position Axis 2
   4-5 - Desired Position Axis 3
   6-7 - Desired Position Axis 4
 Write: 8 total bytes
  Bytes
   0-1 - Desired Position Axis 1
   2-3 - Desired Position Axis 2
   4-5 - Desired Position Axis 3
   6-7 - Desired Position Axis 4
 Initialize: All bytes are set to zero as default.
  The on-board permanent memory is read,
  checksum verification is performed, and
  then if a proper checksum exists then
  all bytes are updated from those
  permanent memory values.
 Each scan cycle the position error is calculated and
 an appropriate adjustment is made to the output
 value. The maximum rate at which that adjustment can
 be made is limited by the MAXIMUM VELOCITY value. A
 value of zero is considered as no-limit.

6. Register: 60
 Name: Maximum Acceleration/Deceleration
 Read: 8 total bytes
  Bytes
   0-1 - Maximum Acc/Decc for Axis 1
   2-3 - Maximum Acc/Decc for Axis 2
   4-5 - Maximum Acc/Decc for Axis 3
   6-7 - Maximum Acc/Decc for Axis 4
 Write: 8 total bytes
  Bytes
   0-1 - Maximum Acc/Decc for Axis 1
   2-3 - Maximum Acc/Decc for Axis 2
   4-5 - Maximum Acc/Decc for Axis 3
   6-7 - Maximum Acc/Decc for Axis 4
 Initialize: All bytes are set to zero as default.
  The on-board permanent memory is read,
  checksum verification is performed, and
  then if a proper checksum exists then
  all bytes are updated from those
  permanent memory values.
 For each scan cycle the position is calculated and an
 appropriate adjustment is made to the output value.
 The rate is limited by the MAXIMUM VELOCITY value.
 Its rate of increase is controlled by the MAXIMUM
 ACC/DECC value. A value of zero is considered no
 limit.

Register: 70
 Name: Response Time
 Read: 4 total bytes
  Bytes
   0 - Response Time for Axis 1
   1 - Response Time for Axis 2
   2 - Response Time for Axis 3
   3 - Response Time for Axis 4
 Write: 4 total bytes
  Bytes
   0 - Response Time for Axis 1
   1 - Response Time for Axis 2
   2 - Response Time for Axis 3
   3 - Response Time for Axis 4
 Initialize: All bytes are set to zero as default.
  The on-board permanent memory is read,
  checksum verification is performed, and
  then if a proper checksum exists then
  all bytes are updated from those
  permanent memory values.
 The position error is calculated at a fixed speed or
 rate. That rate is set by the RESPONSE TIME In
 milliseconds. For each RESPONSE TIME value in
 milliseconds the system calculates the error and
 adjusts the output value.

8. Register: 80
 Name: Actual Output Value
 Read: 8 total bytes
  Bytes
   0-1 - Actual Output for Axis 1
   2-3 - Actual Output for Axis 2
   4-5 - Actual Output for Axis 3
   6-7 - Actual Output for Axis 4
 Write: None
 Initialize: All outputs are set to zero prior to
  the first scan cycle.
 The final output of the control loop is a PWM signal.
 That signal is a 12-bit right justified value that
 determines 'ON' time of total 12-bit count. The
 system clock is used to drive the PWM. The ACTUAL
 OUTPUT is provided for reference purposes only.

9. Register: 90
 Register: A0
 Register: B0
 Register: C0
 Register: D0
 Name: Undefined Register
 Read: 16 total bytes
  Bytes
   0-F - Undefined
 Write: 16 total bytes
  Bytes
   0-F - Undefined
 Initialize: All bytes are set to zero as default.
  The on-board permanent memory is read,
  checksum verification is performed, and
  then if a proper checksum exists then
  all bytes are updated from those
  permanent memory values.
 The above-identified registers are currently undefined
 in the Local Controller Program. As features and
 functions are added to the application these registers
 may be used. Unused registers are 16 bytes in length
 for both read and write. They can be used for
 temporary storage.

The foregoing description of invention so fully reveals the general nature of the invention (including apparatus and methods) that others can readily modify such invention and/or adapt it for various applications without departing from its generic concept, and, therefore such adaptations and modifications should be and are intended to be comprehended within the meaning and range of equivalents of the following claims, which claims define subject matter regarded by us to be our invention.

We claim:

1. A dynamic multivane electron arc beam collimator for defining the electron field of an electron beam emitted by a linear accelerator for use in electron arc therapy, said collimator comprising:

(a) a plurality of vanes positioned and adapted to define an electron aperture which defines said electron field, (b) a plurality of vane movement means associated with said vanes for moving said vanes to dynamically define said electron aperture and to thereby dynamically define said electron field, and (c) a plurality of local controllers to control said vane movement means through distributed processing;

wherein (a), (b) and (c) are adapted to provide vane movement that is independent of the movement of the other vanes and that is capable of movement simultaneous with the movement of the other vanes.

2. A collimator in accordance with claim 1 wherein said vanes are divided into two parallel vane rows to form a plurality of vane pairs; wherein each vane pair is comprised of two opposing vanes which can be moved linearly to dynamically define an opening between said vanes of said pair; and wherein the vane pair openings defined by said vane pairs collectively define said electron aperture.

3. A collimator in accordance with claim 2 wherein the number of said vane pairs ranges from 3 to 71.

4. A collimator in accordance with claim 2 wherein the number of said vane pairs ranges from 5 to 31.

5. A collimator in accordance with claim 2 wherein (a), (b) and (c) are combined to form a unit that is attachable to and detachable from the head of said linear accelerator.

6. A collimator in accordance with claim 2 wherein the number of said vane is an odd number; and wherein the target treatment area is located and centered with respect to the center vane pair.

7. A collimator in accordance with claim 1 wherein each local controller controls one or more of the vane movement means.

8. A collimator in accordance with claim 1 wherein the vane movement means further comprises a vane position monitoring means to monitor the position of the vane associated with the vane movement means.

9. A collimator in accordance with claim 8 wherein the vane position monitoring means is a potentiometer.

10. A collimator in accordance with claim 1 wherein said collimator further comprises a housing for (a), (b) and (c); and wherein said housing is attachable to the head of the linear accelerator and detachable from the head of the linear accelerator.

11. A collimator in accordance with claim 1 wherein said collimator further comprises a noncontact communication means for communication with a remote host controller.

12. A collimator in accordance with claim 11 wherein said noncontact communication means comprises an infra-red transceiver.

13. A collimator in accordance with claim 1 wherein said collimator further comprises a local power source.

14. A collimator in accordance with claim 1 wherein said local controllers are networked as nodes on a common network.

15. A collimator in accordance with claim 1 wherein said vane movement means are local to said vanes.

16. A portable dynamic multivane electron arc beam collimator for defining the electron field of an electron beam emitted by a linear accelerator for use in electron arc therapy, said collimator comprising:
(a) a plurality of vanes positioned and adapted to define an electron aperture which defines said electron field,
(b) a plurality of vane movement means associated with said vanes for moving said vanes to dynamically define said electron aperture and to thereby dynamically define said electron field,
(c) a plurality of local controllers to control said vane movement means, and
(d) a housing; wherein said vanes, vane movement means and local controllers are housed within said housing; wherein said collimator is portable; and wherein said collimator is attachable to and detachable from the head of said linear accelerator.

17. A dynamic multivane electron arc beam collimator for defining the electron field of an electron beam emitted by a linear accelerator for use in electron arc therapy, said collimator comprising:
(a) a plurality of vanes positioned and adapted to define an electron aperture which defines said electron field,
(b) vane movement means for moving said vanes to dynamically define said electron aperture and to thereby dynamically define said electron field, and
(c) a local controller to control said vane movement means and to thereby control movement of said vanes; wherein said vanes, said vane movement means and said local controller are combined to form a unit which is attachable to and detachable from the head of said linear accelerator; and wherein said local controller provides local intelligence to said unit.

18. A dynamic multivane electron arc beam collimation system for defining the electron field of an electron beam emitted by a linear accelerator for use in electron arc therapy, said collimation system comprising;
(a) a dynamic multivane electron arc beam collimator comprising:
(i) a plurality of vanes positioned and adapted to define an electron aperture which defines said electron field,
(ii) a plurality of vane movement means for moving said vanes to dynamically define said electron aperture and to thereby dynamically define said electron field, and
(iii) a plurality of local controllers to control said vane movement means and to thereby control movement of said vanes;
wherein (i), (ii) and (iii) are adapted to provide independent and simultaneous movement of each vane; wherein said vanes are divided into two parallel vane rows to form a plurality of vane pairs; wherein each vane pair is comprised of two opposing vanes which can be moved linearly to dynamically define an opening between said vanes of said pair; and wherein the vane pair openings defined by said vane pairs collectively define said electron aperture.
(b) means for selecting a treatment arc and dividing said treatment arc into a plurality of arc segments defined by reference angles;
(c) means for determining preferred vane pair openings for each arc segment and for representing said preferred vane pair openings as vane position data for each arc segment;
(d) means for monitoring current treatment angle of the linear accelerator during linear accelerator rotation to detect reference angles when encountered by such rotation, and
(e) means for sequentially transmitting to the local controllers of said collimator the vane position data of each arc segment when the reference angle identifying the arc segment is encountered by linear accelerator rotation;
wherein the local controllers are adapted to process the vane position data received by the local controllers: and wherein the local controllers and vane movement means are adapted to cause the vanes to move to the vane positions represented by the vane position data of the arc segments as transmitted to the local controllers during linear accelerator rotation.

* * * * *